United States Patent
Codd et al.

(10) Patent No.: US 7,183,411 B2
(45) Date of Patent: Feb. 27, 2007

(54) NAPHTHOL, QUINOLINE AND ISOQUINOLINE-DERIVED UREA MODULATORS OF VANILLOID VR1 RECEPTOR

(75) Inventors: Ellen Codd, Blue Bell, PA (US); Scott L. Dax, Landenberg, PA (US); Michele Jetter, Norristown, PA (US); Mark McDonnell, Lansdale, PA (US); James J. McNally, Souderton, PA (US); Mark Youngman, Warminster, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 99 days.

(21) Appl. No.: 10/616,579

(22) Filed: Jul. 10, 2003

(65) Prior Publication Data

US 2004/0157865 A1    Aug. 12, 2004

Related U.S. Application Data

(60) Provisional application No. 60/395,951, filed on Jul. 15, 2002, provisional application No. 60/395,728, filed on Jul. 12, 2002.

(51) Int. Cl.
*C07D 217/22* (2006.01)
*A61K 31/47* (2006.01)

(52) U.S. Cl. .................... 546/143; 514/307
(58) Field of Classification Search ........... 546/143; 514/307
See application file for complete search history.

(56) References Cited

U.S. PATENT DOCUMENTS 5,610,192 A    3/1997  Cohen et al.
5,656,634 A *  8/1997  Chang et al. ............... 514/256
2003/0158198 A1* 8/2003 Lee et al. .................... 514/241

FOREIGN PATENT DOCUMENTS

| EP | 418071 | * | 3/1991 |
|---|---|---|---|
| WO | WO 00/71493 A2 | | 11/2000 |
| WO | WO 02/08221 A2 | | 1/2002 |
| WO | WO 02/16317 A1 | | 2/2002 |
| WO | WO 02/16318 A1 | | 2/2002 |
| WO | WO 02/16319 A1 | | 2/2002 |
| WO | WO 03080578 A1 | | 10/2003 |

OTHER PUBLICATIONS

Walpole, C.S.J. et al., "The Discovery of Capsazepine, the First Competitive Antagonist of the Sensory Neuron Excitants Capsaicin and Resinferatoxin." *J. Med. Chem.* 1994, pp. 1942-1954, vol. 37.

Honma, T. et al., Structure-Based Generation of a New Class of Potent Cdk4 Inhibitors: New de Novo Design Strategy and Library Design. *J. Med Chem.*, 2001, pp. 4615-4627, vol. 44.

Garcia-Martinez, C. et al., "Attenuation of thermal nociception and hyperalgesia by VR1 blockers." *PNAS*, 2002, pp. 2374-2379, vol. 99, No. 4.

* cited by examiner

*Primary Examiner*—D. Margaret Seaman

(57) ABSTRACT

This invention is directed to vanilloid receptor VR1 ligands. More particularly, this invention relates to naphthol, quinoline and isoquinoline-derived ureas that are potent antagonists or agonists of VR1 which are useful for the treatment and prevention of inflammatory and other pain conditions in mammals.

5 Claims, No Drawings

NAPHTHOL, QUINOLINE AND ISOQUINOLINE-DERIVED UREA MODULATORS OF VANILLOID VR1 RECEPTOR

CROSS-REFERENCE TO RELATED APPLICATIONS

This application claims priority to U.S. Provisional Patent Application Nos. 60/395,728 and 60/395,951, filed Jul. 12, 2002 and Jul. 15, 2002, respectively, which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

This invention is directed to novel vanilloid receptor VR1 ligands. More particularly, this invention relates to novel naphthol, quinoline and isoquinoline-derived ureas that are potent antagonists or agonists of VR1 and exhibit activity in animal models of hyperalgesia and colitis, and are useful for the treatment and prevention of pain conditions in humans including arthritis, and for the treatment of irritable-bowel syndrome and associated conditions.

Noxious chemical, thermal and mechanical stimuli excite peripheral nerve endings of small diameter sensory neurons (nociceptors) in sensory ganglia (e.g., dorsal root, nodose and trigeminal ganglia) and initiate signals that are perceived as pain. These neurons are crucial for the detection of harmful or potentially harmful stimuli (heat) and tissue damage (local tissue acidosis and/or stretch) that arise from changes in the extracellular space during inflammatory or ischaemic conditions (Wall, P. D., and Melzack, R., *Textbook of Pain*, 1994, New York: Churchill Livingstone). Nociceptors transduce noxious stimuli into membrane depolarization that triggers action potential, conducts the action potential from the sensory sites to the synapses in the CNS, and conversion of action potentials invokes a perception of pain, discomfort, and appropriate mechanical/physical protective reflexes. At the molecular level, nociception is carried out by ion channels or receptors. Plant derived vanilloid compounds (capsaicin and its ultrapotent analog, resiniferatoxin, etc.) are known to selectively depolarize nociceptors and elicit sensations of burning pain—the sensation that is typically obtained by hot chili peppers. Therefore, capsaicin mimics the action of physiological/endogenous stimuli that activates the "nociceptive pathway". Recent advances in pain biology have identified receptors for vanilloids, protons (i.e., acidic solutions), and for heat. Because nociceptors are involved with unwanted pain and inflammatory conditions in human beings and animals, modulation of their nociceptive pathway is important in palliative and other therapies.

Walpole and colleagues at Sandoz reported on the first competitive antagonist of the sensory neuron excitants capsaicin and resineriferatoxin (Walpole, C. S. J. et. al., *J. Med. Chem*. 1994, 37, 1942). Subsequently, capsazepine has been shown to be a vanilloid receptor antagonist. Capsazepine, however, is not naphthol, quinoline and isoquinoline-derived. Jee Woo Lee and colleagues at Pacific Corporation disclosed thiocarbamic acid derived VR1 antagonists in WO0216317A1 and vanilloid receptor modulators in WO0216318A1 and WO0216319A1 but these applications do not disclose or describe N-naphthol, quinoline and isoquinoline-derived N'-benzylic ureas. Hutchinson and colleagues at Neurogen describe diaryl piperazinyl ureas and related compounds as capsaicin receptor ligands in WO02082212A1 but N-naphthol, quinoline and isoquinoline-derived N'-benzylic ureas are not covered. Scientists at the Universidad Miguel Hernandez in Alicante, the Universidad de Valencia and the Consejo Superior de Investigaciones Cientificas (CSIC) in Barcelona have used a combinatorial chemistry-based approach to discover compounds that modulate the vanilloid VR1 receptor and have disclosed two trialkylglycine-based compounds as noncompetitive VR1 channel blockers (Garcia-Martinez, C. et al. Proc Natl Acad Sci USA 2002, 99(4): 2374) but none are naphthol, quinoline and isoquinoline-derived.

Honma et al. disclose various urea compounds as Cdk4 inhibitors, including unsubstituted 5-naphth-3-ol-benzyl urea (J. Med. Chem. 2001, 44, 4615–4627). They do not, however, describe or suggest these or any other compounds as being modulators of VR and they do not describe or suggest the compounds of the present invention.

U.S. Pat. No. 6,001,860 discloses various bis-aryl and aryl arylalkyl ureas as inhibitors of acyl coenzyme A: cholesterol acyl transferase. This patent also does not describe or suggest these or any other compounds as being modulators of VR and does not describe or suggest the compounds of the present invention.

International patent publication number WO 00/71493A2 very broadly describes bis alkyl aryl and heteroaryl linked compounds, including urea moieties as linkers. These compounds are characterized as inhibitors of factor Xa. However, this publication does not describe or suggest these or any other compounds as being modulators of VR and does not describe or suggest the compounds of the present invention.

U.S. Pat. No. 5,610,192 very broadly describes bis aryl and heteroaryl linked compounds, including urea moieties as linkers. These compounds are characterized as inhibitors of metazoan parasite proteases. However, this patent also does not describe or suggest these or any other compounds as being modulators of VR and does not describe or suggest the compounds of the present invention.

Thus, there is a need for potent modulators of VR, and in particular, for novel naphthol, quinoline and isoquinoline-derived ureas that exhibit potent binding affinity for the human and rat VR1 ion channel. There is also a need for novel naphthol, quinoline and isoquinoline-derived ureas that act as potent functional antagonists and/or agonists of the human and rat VR1 ion channel. Finally, there is a need for novel naphthol, quinoline and isoquinoline-derived ureas that bind with high affinity to VR1 and also act as potent functional antagonists of the human and rat VR1 ion channel.

SUMMARY OF THE INVENTION

The present invention is directed to compositions comprising a compound of Formula (I) and Formula (II):

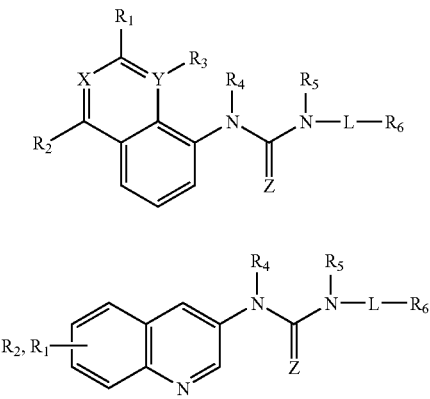

Formula (I)

Formula (II)

wherein:
R₁ and R₂ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; formyl;
R₃ is independently selected from the group consisting of hydrogen; hydroxy; fluoro; and chloro; nitro; amino; $C_{1-8}$alkanylamino, and $C_{1-8}$dialkanylamino;
L is $C_{2-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;
R₄ is selected from the group consisting of hydrogen and $C_{1-3}$alkanyl;
R₅ is selected from the group consisting of hydrogen and $C_{1-3}$alkanyl;
R₆ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;
X is selected from C—H, N and N->O;
Y is C or N, provided that if Y is N then R₃ is absent;
Z is selected from the group consisting of O and S; and
enantiomers, diastereomers, tautomers, solvates, and pharmaceutically acceptable salts thereof.

The present invention is also directed to compositions comprising a compound of Formula (III):

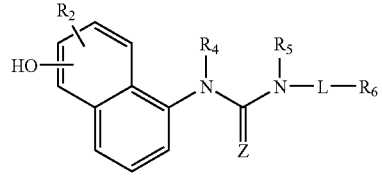

Formula (III)

wherein:
R₂ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; formyl;
L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;
R₄ is selected from the group consisting of hydrogen and $C_{1-3}$alkanyl;
R₅ is selected from the group consisting of hydrogen and $C_{1-3}$alkanyl;
R₆ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

Z is selected from the group consisting of O and S; and enantiomers, diastereomers, tautomers, solvates, and pharmaceutically acceptable salts thereof.

The present invention is further directed to compositions comprising a compound of Formula (IV):

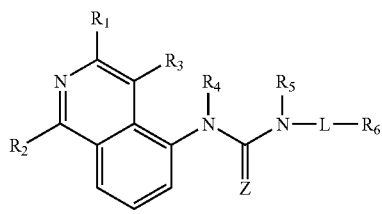

Formula (IV)

wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of, morpholinyl, piperazinyl, piperidinyl, imidazolidinyl, pyrazolidinyl, thiomorpholinyl, and pyrrolidinyl;

Z is selected from the group consisting of O and S; and enantiomers, diastereomers, tautomers, solvates, and pharmaceutically acceptable salts thereof.

Finally, the present invention is directed to pharamceutical compositions containing compounds of Formula (I), Formula (II), Formula (III), and Formula (IV) as well as to methods of treatment of diseases and conditions by administration of these compositions, and also to pharmaceutical kits containing them.

DETAILED DESCRIPTION OF THE INVENTION

As used herein, the following underlined terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

"Fluorinated alkyl" refers to a saturated branched or straight chain hydrocarbon radical derived by removal of 1 hydrogen atom from the parent alkane; the parent alkane contains from 1 to 6 carbon atoms with 1 or more hydrogen atoms substituted with fluorine atoms up to and including substitution of all hydrogen atoms with fluorine. Preferred fluorinated alkyls include trifluoromethyl substituted alkyls and perfluorinated alkyls; more preferred fluorinated alkyls include trifluoromethyl, perfluoroethyl, 2,2,2-trifluoroethyl, perfluoropropyl, 3,3,3-trifluoroprop-1-yl, 3,3,3-trifluoroprop-2-yl, 1,1,1,3,3,3-hexafluoroprop-2-yl; a particularly preferred fluorinated alkyl is trifluoromethyl.

"Fluorinated alkanyloxy" refers to a radical derived from a fluorinated alkyl radical attached to an oxygen atom with the oxygen atom having one open valence for attachment to a parent structure.

"Alkyl:" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl", "alkenyl" and/or "alkynyl" is used, as defined below. In preferred embodiments, the alkyl groups are $(C_{1-8})$ alkyl, with $(C_{1-3})$ being particularly preferred.]

"Alkanyl:" refers to a saturated branched, straight-chain or cyclic monovalent hydrocarbon radical derived by the removal of one hydrogen atom from a single carbon atom of a parent alkane. Typical alkanyl groups include, but are not limited to, methanyl; ethanyl; propanyls such as propan-1-yl, propan-2-yl, cyclopropan-1-yl, etc.; butyanyls such as butan-1-yl, butan-2-yl, 2-methyl-propan-1-yl, 2-methyl-propan-2-yl, cyclobutan-1-yl, etc.; and the like. In preferred embodiments, the alkanyl groups are $(C_{1-8})$ alkanyl, with $(C_{1-3})$ being particularly preferred.

"Alkenyl:" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is $(C_{2-8})$ alkenyl, with $(C_{2-3})$ being particularly preferred.

"Alkynyl:" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is $(C_{2-8})$ alkynyl, with $(C_{2-3})$ being particularly preferred.

"Alkyldiyl:" refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methylprop-2-en-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkyndiyl is used. In preferred embodiments, the alkyldiyl group is $(C_{1-8})$ alkyldiyl, with $(C_{1-8})$ being particularly preferred. Also preferred are saturated acyclic alkandiyl radicals in which the radical centers are at the terminal carbons, e.g., methandiyl; ethan-1,2-diyl; propan-1,3-diyl; butan-1,4-diyl; and the like (also referred to as alkylenos, as defined infra).

"Vic Alkyidiyl:" refers to a saturated or unsaturated, branched, straight-chain or cyclic hydrocarbon radical having two adjacent monovalent radical centers derived by the removal of one hydrogen atom from each of two adjacent carbon atoms of a parent alkane, alkene or alkyne. The two monovalent radical centers can form bonds with the same or different atom(s). Typical vic alkyldiyls include, but are not limited to vic ethyldiyls such as ethan-1,2-diyl, ethen-1,2-diyl; vic propyldiyls such as propan-1,2-diyl, cyclopropan-1,2-diyl, prop-1-en-1,2-diyl, prop-2-en-1,2-diyl, cycloprop-1-en-1,2-diyl, etc.; vic butyldiyls such as butan-1,2-diyl, 2-methyl-propan-1,2-diyl, cyclobutan-1,2-diyl, but-1-en-1,2-diyl, cyclobut-1-en-1,2-diyl, buta-1,3-dien-1,2-diyl, cyclobuta-1,3-dien-1,2-diyl, but-3-yn-1,2-diyl, etc.; and the like. Where specific levels of saturation are intended, the nomenclature vic alkandiyl, vic alkendiyl and/or vic alkyndiyl is used. In preferred embodiments, the vic alkyldiyl group is $(C_{2-8})$ vic alkyldiyl, with $(C_{2-3})$ being particularly preferred.

"Gem Alkyldiyl:" refers to a saturated or unsaturated, branched, straight-chain or cyclic hydrocarbon radical having one divalent radical center derived by the removal of two hydrogen atoms from a single carbon atom of a parent alkane, alkene or alkyne. The divalent radical center forms bonds with two different atoms. Typical gem alkyldiyls include, but are not limited to gem methanyldiyl; gem ethyldiyls such as ethan-1,1-diyl, ethen-1,1-diyl; gem propyldiyls such as propan-1,1-diyl, propan-2,2-diyl, cyclopropan-1,1-diyl, prop-1-en-1,1-diyl, cycloprop-2-en-1,1-diyl, prop-2-yn-1,1-diyl, etc.; butyldiyls such as butan-1,1-diyl, butan-2,2-diyl, 2-methyl-propan-1,2-diyl, cyclobutan-1,1-diyl, but-1-en-1,1-diyl, 2-methyl-prop-1-en-1,1-diyl, 2-methyl-prop-2-en-1,1-diyl, cyclobut-2-en-1,1-diyl, buta-1,3-dien-1,1-diyl, etc.; and the like. Where specific levels of saturation are intended, the nomenclature gem alkandiyl, gem alkendiyl and/or gem alkyndiyl is used. In preferred embodiments, the gem alkyldiyl group is $(C_{1-6})$ gem alkyldiyl, with $(C_{1-3})$ being particularly preferred.

"Alkyleno:" refers to a saturated or unsaturated, straight-chain or branched acyclic bivalent hydrocarbon bridge radical derived by the removal of one hydrogen atom from each of the two terminal carbon atoms of an acyclic parent alkane, alkene or alkyne. Typical alkyleno groups include, but are not limited to, methano; ethylenos such as ethano, etheno, ethyno; propylenos such as propano, propeno, prop-1,2-dieno, propyno, etc.; butylenos such as butano, 2-methyl-propano, but-1-eno, but-2-eno, 2-methyl-prop-1-eno, 2-methanylidene-propano, but-1,3-dieno, but-1-yno, but-2-yno, but-1,3-diyno, etc.; and the like. Where specific levels of saturation are intended, the nomenclature alkano, alkeno and/or alkyno is used. In preferred embodiments, the alkyleno group is $(C_{1-8})$ alkyleno, with $(C_{1-3})$ being particularly preferred. Also preferred are straight-chain saturated alkano radicals, e.g., methano, ethano, propano, butano, and the like.

"Alkylidene:" refers to a saturated or unsaturated, branched, straight-chain or cyclic divalent hydrocarbon radical derived by removal of two hydrogen atoms from the same carbon atom of a parent alkane, alkene or alkyne. The divalent radical center forms a double bond with a single atom. Typical alkylidene radicals include, but are not limited to, methanylidene, ethylidenes such as ethanylidene, ethenylidene; propylidenes such as propan-1-ylidene, propan-2-ylidene, cyclopropan-1-ylidene, prop-1-en-1-ylidene, prop-2-en-1-ylidene, cycloprop-2-en-1-ylidene, etc.; butylidenes such as butan-1-ylidene, butan-2-ylidene, 2-methyl-propan-1-ylidene, cyclobutan-1-ylidene, but-1-en-1-ylidene, but-2-en-1-ylidene, but-3-en-1-ylidene, buta-1,3-dien-1-ylidene; cyclobut-2-en-1-ylidene, etc.; and the like. Where specific levels of saturation are intended, the nomenclature alkanylidene, alkenylidene and/or alkynylidene is used. In preferred embodiments, the alkylidene group is $(C_{1-8})$ alkylidene, with $(C_{1-3})$ being particularly preferred. Also preferred are acyclic saturated alkanylidene radicals in which the divalent radical is at a terminal carbon, e.g., methanylidene, ethan-1-ylidene, propan-1-ylidene, butan-1-ylidene, 2-methyl-propan-1-ylidene, and the like.

"Alkylidyne:" refers to a saturated or unsaturated, branched or straight-chain trivalent hydrocarbon radical derived by removal of three hydrogen atoms from the same carbon atom of a parent alkane, alkene or alkyne. The trivalent radical center forms a triple bond with a single atom. Typical alkylidyne radicals include, but are not limited to, methanylidyne; ethanylidyne; propylidynes such as propan-1-ylidyne, prop-2-en-1-ylidyne, prop-2-yn-1-ylidyne; butylidynes such as butan-1-ylidyne, 2-methyl-propan-1-ylidyne, but-2-en-1-ylidyne, but-3-en-1-ylidyne, buta-2,3-dien-1-ylidyne, but-2-yn-1-ylidyne, but-3-yn-1-ylidyne, etc.; and the like. Where specific levels of saturation are intended, the nomenclature alkanylidyne, alkenylidyne and/or alkynylidyne is used. In preferred embodiments, the alkylidyne group is $(C_{1-8})$ alkylidyne, with $(C_{1-3})$ being particularly preferred. Also preferred are saturated alkanylidyne radicals, e.g., methanylidyne, ethanylidyne, propan-1-ylidyne, butan-1-ylidyne, 2-methyl-propan-1-ylidyne, and the like.

"Heteroalkyl, Heteroalkanyl, Heteroalkenyl, Heteroalkynyl, Heteroalkylidene, Heteroalkylidyne, Heteroalkyldiyl, Vic Heteralkyldiyl, Gem Heteroalkyldiyl, Heteroalkyleno and Heteroalkyldiylidene:" refer to alkyl, alkanyl, alkenyl, alkynyl, alkylidene, alkylidyne, alkyldiyl, vic alkyldiyl, gem alkyldiyl, alkyleno and alkyldiylidene radicals, respectively, in which one or more carbon atoms (and any necessary associated hydrogen atoms) are independently replaced with the same or different heteroatoms (including any necessary hydrogen or other atoms). Typical heteroatoms to replace the carbon atom(s) include, but are not limited to, N, P, O, S, Si, etc. Preferred heteroatoms are O, N and S. Thus, heteroalkyl, heteroalkanyl, heteroalkenyl, heteroalkynyl, heteroalkylidene, heteroalkylidyne, heteroalkyldiyl, vic heteroalkyldiyl, gem heteroalkyldiyl, heteroalkyleno and heteroalkyldiylidene radicals can contain one or more of the same or different heteroatomic groups, including, by way of example and not limitation, epoxy (—O—), epidioxy (—O—O—), thioether (—S—), epidithio (—SS—), epoxythio (—O—S—), epoxyimino (—O—NR'—), imino (—NR'—), biimmino (—NR'—NR'—), azino (=N—N=), azo (—N=N—), azoxy (—N—O—N—), azimino (—NR'—N=N—), phosphano (—PH—), $\lambda^4$-sulfano (—SH$_2$—), sulfonyl (—S(O)$_2$—), and the like, where each R' is independently hydrogen or $(C_1$–$C_6)$ alkyl.

"Parent Aromatic Ring System:" refers to an unsaturated cyclic or polycyclic ring system having a conjugated π electron system. Specifically included within the definition of "parent aromatic ring system" are fused ring systems in which one or more rings are aromatic and one or more rings are saturated or unsaturated, such as, for example, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like "Ary:" refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In preferred embodiments, the aryl group is $(C_{5-20})$ aryl, with $(C_{5-10})$ being particularly preferred. Particularly preferred aryl groups are phenyl and naphthyl groups.

"Arylalkyl:" refers to an acyclic alkyl group in which one of the hydrogen atoms bonded to a carbon atom, typically a terminal carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. [In preferred embodiments, the arylalkyl group is $(C_{6-26})$ arylalkyl, e.g., the alkanyl, alkenyl or alkynyl moiety of the arylalkyl group is $(C_{1-6})$ and the aryl moiety is $(C_{5-20})$. In particularly preferred embodiments the arylalkyl group is $(C_{6-13})$, e.g., the alkanyl, alkenyl or alkynyl moiety of the arylalkyl group is $(C_{1-3})$ and the aryl moiety is $(C_{5-10})$. Even more preferred arylalkyl groups are phenylalkanyls.

"Alkanyloxy:" refers to a saturated branched, straight-chain or cyclic monovalent hydrocarbon alcohol radical derived by the removal of the hydrogen atom from the hydroxide oxygen of the alcohol. Typical alkanyloxy groups include, but are not limited to, methanyl; ethanyloxy; propanyloxy groups such as propan-1-yloxy $(CH_3CH_2CH_2O—)$, propan-2-yloxy $((CH_3)_2CHO—)$, cyclopropan-1-yloxy, etc.; butyanyloxy groups such as butan-1-yloxy, butan-2-yloxy, 2-methyl-propan-1-yloxy, 2-methyl-propan-2-yloxy, cyclobutan-1-yloxy, etc.; and the like. In preferred embodiments, the alkanyloxy groups are $(C_{1-8})$ alkanyloxy groups, with $(C_{1-3})$ being particularly preferred.

"Parent Heteroaromatic Ring System:" refers to a parent aromatic ring system in which one or more carbon atoms are each independently replaced with a heteroatom. Typical heteratoms to replace the carbon atoms include, but are not limited to, N, P, O, S, Si etc. Specifically included within the definition of "parent heteroaromatic ring systems" are fused ring systems in which one or more rings are aromatic and one or more rings are saturated or unsaturated, such as, for example, arsindole, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl:" refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In preferred embodiments, the heteroaryl group is a 5–20 membered heteroaryl, with 5–10 membered heteroaryl being particularly preferred. Specific preferred heteroaryls for the present invention are quinoline, isoquinoline, pyridine, pyrimidine, furan, thiophene and imidazole.

"Substituted:" refers to a radical in which one or more hydrogen atoms are each independently replaced with the same or different substituent(s). Typical substituents include, but are not limited to, —X, —R, —O$^-$, =O, —OR, —O—OR, —SR, —S$^-$, =S, —NRR, =NR, —CX$_3$, —CN, —OCN, —SCN, —NCO, —NCS, —NO, —NO$_2$, =N$_2$, —N$_3$, —NHOH, —S(O)$_2$O$^-$, —S(O)$_2$OH, —S(O)$_2$R, —P(O)(O$^-$)$_2$, —P(O)(OH)$_2$, —C(O)R, —C(O)X, —C(S)R, —C(S)X, —C(O)OR, —C(O)O$^-$, —C(S)OR, —C(O)SR, —C(S)SR, —C(O)NRR, —C(S)NRR and —C(NR)NRR, where each X is independently a halogen (preferably —F, —Cl or —Br) and each R is independently —H, alkyl, alkanyl, alkenyl, alkynyl, alkylidene, alkylidyne, aryl, arylalkyl, arylheteroalkyl, heteroaryl, heteroarylalkyl or heteroaryl-heteroalkyl, as defined herein. Preferred substituents include hydroxy, halogen, C$_{1-8}$alkyl, C$_{1-8}$alkanyloxy, fluorinated alkanyloxy, fluorinated alkyl, C$_{1-8}$alkylthio, C$_{3-8}$cycloalkyl, C$_{3-8}$cycloalkanyloxy, nitro, amino, C$_{1-8}$alkylamino, C$_{1-8}$dialkylamino, C$_{3-8}$cycloalkylamino, cyano, carboxy, C$_{1-7}$alkanyloxycarbonyl, C$_{1-7}$alkylcarbonyloxy, formyl, carbamoyl, phenyl, aroyl, carbamoyl, amidino, (C$_{1-8}$alkylamino)carbonyl, (arylamino)carbonyl and aryl(C$_{1-8}$alkyl)carbonyl.

"Aroyl" refers to arylacyl substituents.

"Acyl" refers to alkylcarbonyl substituents.

With reference to substituents, the term "independently" means that when more than one of such substituent is possible, such substituents may be the same or different from each other.

Throughout this disclosure, the terminal portion of the designated side chain is described first, followed by the adjacent functionality toward the point of attachment. Thus, for example, a "phenylC$_{1-6}$alkanylaminocarbonylC$_{1-6}$alkyl" substituent refers to a group of the formula

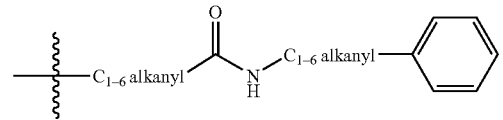

The present invention is directed to compounds of Formula (I):

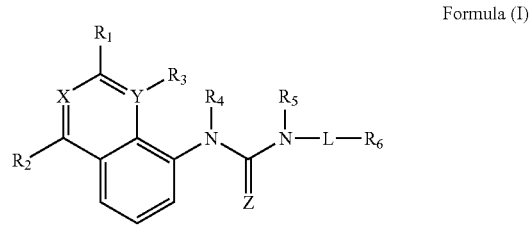

wherein:
R$_1$ and R$_2$ are substituents independently selected from the group consisting of hydrogen; hydroxy; halogen; C$_{1-8}$alkanyl optionally substituted with one or more substituents independently selected from the group consisting of halogen, fluorinated alkanyl and C$_{1-8}$alkanyloxy; C$_{1-8}$alkanyloxy optionally substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; C$_{1-7}$alkanylaminocarbonyl; C$_{1-7}$alkanylcarbonylamino; diC$_{1-7}$alkanylaminocarbonyl; and formyl;

R$_3$ is independently selected from the group consisting of hydrogen; hydroxy; fluoro; chloro; nitro; amino; C$_{1-8}$alkanylamino, and C$_{1-8}$dialkanylamino;

L is a C$_{1-4}$alkyldiyl optionally substituted with a substituent selected from the group consisting of C$_{1-8}$alkanyl, C$_{3-8}$cycloalkanyl and phenyl optionally substituted with one to three substituents independently selected from the group consisting of C$_{1-8}$alkanyl, halogen, C$_{1-8}$alkanyloxy, hydroxy, fluorinated alkanyl, fluorinated alkanyloxy, amino, di(C$_{1-3}$)alkanylamino, and C$_{1-3}$alkanylamino;

R$_4$ is selected from the group consisting of hydrogen and C$_{1-3}$alkanyl;

R$_5$ is selected from the group consisting of hydrogen and C$_{1-3}$alkanyl;

R$_6$ is selected from the group consisting of phenyl substituted with one to three substituents independently selected from the group consisting of C$_{1-8}$alkanyl, C$_{3-8}$cycloalkanyl, halogen, C$_{1-8}$alkanyloxy, hydroxy, fluorinated alkanyl, fluorinated alkanyloxy, nitro, amino, di(C$_{1-8}$)alkanylamino, C$_{1-8}$alkanylamino, aminosulfonyl, C$_{1-8}$alkanylaminosulfonyl, di(C$_{1-8}$)alkanylaminosulfonyl and cyano; naphthyl optionally substituted with one to three substituents independently selected from the group consisting of C$_{1-8}$alkanyl, halogen, C$_{1-8}$alkanyloxy, hydroxy, fluorinated alkanyl, fluorinated alkanyloxy, nitro, amino, di(C$_{1-8}$)alkanylamino, C$_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;
Y is C or N, provided that if Y is N then $R_3$ is absent;
Z is selected from the group consisting of O and S; and enantiomers, diastereomers, tautomers, solvates, and pharmaceutically acceptable salts thereof.

Preferred compounds of Formula (I) are those wherein Y is C. Other preferred compounds of Formula (I) are those wherein:

(1) $R_1$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

(2) more preferably, $R_1$ is a substituent independently selected from the group consisting of hydrogen; hydroxy; halogen; and $C_{1-8}$alkanyl;

(3) even more preferably, $R_1$ is a substituent independently selected from the group consisting of hydrogen; hydroxy; methyl; and chloro;

(4) $R_2$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

(5) more preferably $R_2$ is hydrogen or halogen;

(6) even more preferably, $R_2$ is hydrogen or chloro;

(7) $R_3$ is independently selected from the group consisting of hydrogen; hydroxy; fluoro; and chloro;

(8) more preferably $R_3$ is hydrogen;

(9) L is $C_{1-4}$alkandiyl optionally substituted with a substituent selected from the group consisting of $C_{1-8}$alkanyl, $C_{3-8}$cycloalkanyl and phenyl;

(10) more preferably L is $C_{1-4}$alkandiyl optionally substituted with a substituent selected from the group consisting of $C_{3-8}$cycloalkanyl and phenyl;

(11) even more preferably L is —$CH_2$— and —$CH_2CH_2$— optionally substituted with a substituent selected from the group consisting of $C_{3-8}$cycloalkanyl and phenyl;

(12) even more preferably L is —$CH_2$—;

(13) $R_4$ is hydrogen;

(14) $R_5$ is hydrogen;

(15) $R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy; naphthyl optionally substituted with one to three substituents independently selected from the group consisting of $C_{1-8}$alkanyl, chloro, fluoro, $C_{1-8}$alkanyloxy, fluorinated alkanyl, and fluorinated alkanyloxy; and thienyl optionally substituted with one to two substituents selected from the group consisting of $C_{1-8}$alkanyl, chloro, fluoro, $C_{1-8}$alkanyloxy, fluorinated alkanyl, and fluorinated alkanyloxy;

(16) preferably, $R_6$ is phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy;

(17) even more preferably, $R_6$ is phenyl substituted with one to three substituents independently selected from the group consisting of t-butyl, chloro, fluoro, methoxy, trifluoromethyl, and trifluoromethoxy;

(18) Z is O; and combinations of (1) through (18), above.

The present invention is also directed to compounds of Formula (II):

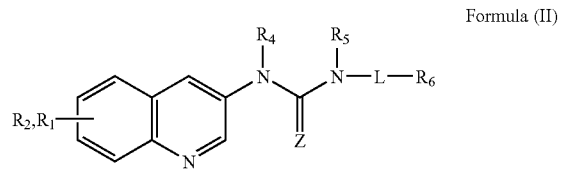

Formula (II)

wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is a $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di(C$_{1-8}$)alkanylamino, C$_{1-8}$alkanylamino, aminosulfonyl, C$_{1-8}$alkanylaminosulfonyl, di(C$_{1-8}$)alkanylaminosulfonyl and cyano; heteroaryl optionally substituted with one to two substituents selected from the group consisting of C$_{1-8}$alkanyl, halogen, C$_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; C$_{5-7}$cycloalkanyl optionally substituted with C$_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then R$_3$ is absent;

Z is selected from the group consisting of O and S; and enantiomers, diastereomers, tautomers, solvates, and pharmaceutically acceptable salts thereof.

Preferred compounds of formula (II) are those wherein:
(1) R$_1$ is a substituent independently selected from the group consisting of hydrogen; hydroxy; halogen; and C$_{1-8}$alkanyl optionally substituted with one or more substituents independently selected from the group consisting of halogen, fluorinated alkanyl and C$_{1-8}$alkanyloxy;
(2) more preferably, R$_1$ is a substituent independently selected from the group consisting of hydrogen; hydroxy; halogen; and C$_{1-8}$alkanyl;
(3) even more preferably, R$_1$ is a substituent independently selected from the group consisting of hydrogen; hydroxy; methyl; and chloro;
(4) R$_2$ is a substituent independently selected from the group consisting of hydrogen; hydroxy; halogen; and C$_{1-8}$alkanyl optionally substituted with one or more substituents independently selected from the group consisting of halogen, fluorinated alkanyl and C$_{1-8}$alkanyloxy;
(5) more preferably R$_2$ is hydrogen or halogen;
(6) even more preferably, R$_2$ is hydrogen or chloro;
(7) L is C$_{1-4}$alkandiyl optionally substituted with a substituent selected from the group consisting of C$_{1-8}$alkanyl, C$_{3-8}$cycloalkanyl and phenyl;
(8) more preferably L is C$_{1-4}$alkandiyl optionally substituted with a substituent selected from the group consisting of C$_{3-8}$cycloalkanyl and phenyl;
(9) even more preferably L is —CH$_2$— and —CH$_2$CH$_2$— optionally substituted with a substituent selected from the group consisting of C$_{3-8}$cycloalkanyl and phenyl;
(10) even more preferably L is —CH$_2$—;
(11) R$_4$ is hydrogen;
(12) R$_5$ is hydrogen;
(13) R$_6$ is selected from the group consisting of phenyl substituted with one to three substituents independently selected from the group consisting of C$_{1-8}$alkanyl, chloro, fluoro, C$_{1-8}$alkanyloxy, fluorinated alkanyl, and fluorinated alkanyloxy; naphthyl optionally substituted with one to three substituents independently selected from the group consisting of C$_{1-8}$alkanyl, chloro, fluoro, C$_{1-8}$alkanyloxy, fluorinated alkanyl, and fluorinated alkanyloxy; and thienyl optionally, substituted with one to two substituents selected from the group consisting of C$_{1-8}$alkanyl, chloro, fluoro, C$_{1-8}$alkanyloxy, fluorinated alkanyl, and fluorinated alkanyloxy;
(14) preferably, R$_6$ is phenyl substituted with one to three substituents independently selected from the group consisting of C$_{1-8}$alkanyl, chloro, fluoro, C$_{1-8}$alkanyloxy, fluorinated alkanyl, and fluorinated alkanyloxy;
(15) even more preferably, R$_6$ is phenyl substituted with one to three substituents independently selected from the group consisting of t-butyl, chloro, fluoro, methoxy, trifluoromethyl, and trifluoromethoxy;
(16) Z is O; and combinations of (1) through (16), above.

The present invention is further directed to compounds of Formula (III):

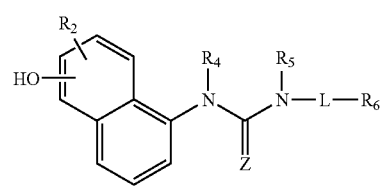

Formula (III)

wherein:

R$_2$ is one to three substituents independently selected from the group consisting of hydrogen; hydroxy; halogen; C$_{1-8}$alkanyl optionally substituted with one or more substituents independently selected from the group consisting of halogen, fluorinated alkanyl and C$_{1-8}$alkanyloxy; C$_{1-8}$alkanyloxy optionally substituted with one or more substituents independently selected from the group consisting of halogen, fluorinated alkanyl and C$_{1-8}$alkanyloxy; fluorinated alkanyloxy; fluorinated alkanyl; C$_{1-8}$alkanylthio optionally substituted with one or more substituents independently selected from the group consisting of halogen, fluorinated alkanyl and C$_{1-8}$alkanyloxy; C$_{3-8}$cycloalkanyl; C$_{3-8}$cycloalkanyloxy; nitro; amino; C$_{1-8}$alkanylamino; C$_{1-8}$dialkanylamino; C$_{3-8}$cycloalkanylamino; cyano; carboxy; C$_{1-7}$alkanyloxycarbonyl; C$_{1-7}$alkanylcarbonyloxy; C$_{1-7}$alkanylaminocarbonyl; C$_{1-7}$alkanylcarbonylamino; diC$_{1-7}$alkanylaminocarbonyl; and formyl;

L is C$_{1-4}$alkyldiyl optionally substituted with a substituent selected from the group consisting of C$_{1-8}$alkanyl, C$_{3-8}$cycloalkanyl and phenyl optionally substituted with one to three substituents independently selected from the group consisting of C$_{1-8}$alkanyl, halogen, C$_{1-8}$alkanyloxy, hydroxy, fluorinated alkanyl, fluorinated alkanyloxy, amino, di(C$_{1-3}$)alkanylamino, and C$_{1-3}$alkanylamino;

R$_4$ is selected from the group consisting of hydrogen and C$_{1-3}$alkanyl;

R$_5$ is selected from the group consisting of hydrogen and C$_{1-3}$alkanyl;

R$_6$ is selected from the group consisting of phenyl substituted with one to three substituents independently selected from the group consisting of C$_{1-8}$alkanyl, C$_{3-8}$cycloalkanyl, halogen, C$_{1-8}$alkanyloxy, hydroxy, fluorinated alkanyl, fluorinated alkanyloxy, nitro, amino, di(C$_{1-8}$)alkanylamino, C$_{1-8}$alkanylamino, aminosulfonyl, C$_{1-8}$alkanylaminosulfonyl, di(C$_{1-8}$)alkanylaminosulfonyl and cyano; naphthyl optionally substituted with one to three substituents independently selected from the group consisting of C$_{1-8}$alkanyl, halogen, C$_{1-8}$alkanyloxy, hydroxy, fluorinated alkanyl, fluorinated alkanyloxy, nitro, amino, di(C$_{1-8}$)alkanylamino, C$_{1-8}$alkanylamino, aminosulfonyl, C$_{1-8}$alkanylaminosulfonyl, di(C$_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl; piperazinyl, piperidinyl, imidazolidinyl, pyrazolidinyl, thiomorpholinyl, and pyrrolidinyl;

Z is selected from the group consisting of O and S; and enantiomers, diastereomers, tautomers, solvates, and pharmaceutically acceptable salts thereof.

Preferred compounds of formula (III) are those wherein:

(1) $R_2$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

(2) more preferably $R_2$ is hydrogen or halogen;

(3) even more preferably, $R_2$ is hydrogen or chloro;

(4) L is $C_{1-4}$alkandiyl optionally substituted with a substituent selected from the group consisting of $C_{1-8}$alkanyl, $C_{3-8}$cycloalkanyl and phenyl;

(5) more preferably L is $C_{1-4}$alkandiyl optionally substituted with a substituent selected from the group consisting of $C_{3-8}$cycloalkanyl and phenyl;

(6) even more preferably L is —CH$_2$— and —CH$_2$CH$_2$— optionally substituted with a substituent selected from the group consisting of $C_{3-8}$cycloalkanyl and phenyl;

(7) even more preferably L is —CH$_2$—;

(8) $R_4$ is hydrogen;

(9) $R_5$ is hydrogen;

(10) $R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy; naphthyl optionally substituted with one to three substituents independently selected from the group consisting of $C_{1-8}$alkanyl, chloro, fluoro, $C_{1-8}$alkanyloxy, fluorinated alkanyl, and fluorinated alkanyloxy; and thienyl optionally substituted with one to two substituents selected from the group consisting of $C_{1-8}$alkanyl, chloro, fluoro, $C_{1-8}$alkanyloxy, fluorinated alkanyl, and fluorinated alkanyloxy;

(11) preferably, $R_6$ is phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy;

(12) even more preferably, $R_6$ is phenyl substituted with one to three substituents independently selected from the group consisting of t-butyl, chloro, fluoro, methoxy, trifluoromethyl, and trifluoromethoxy;

(13) Z is O; and combinations of (1) through (1.3), above.

The present invention is also directed to compounds of Formula (IV):

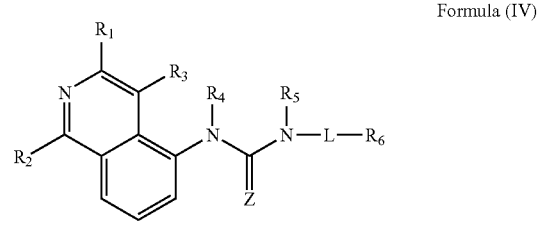

Formula (IV)

wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

Z is selected from the group consisting of O and S; and enantiomers, diastereomers, tautomers, solvates, and pharmaceutically acceptable salts thereof.

The present invention is also directed to compositions comprising a compound of Formula (V):

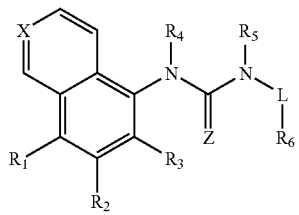

Formula (V)

wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; and chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is N or N->O;

Z is selected from the group consisting of O and S; and enantiomers, diastereomers, tautomers, solvates, and pharmaceutically acceptable salts thereof.

Preferred compounds of Formulas (IV) and (V) are those wherein:

(1) $R_1$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

(2) more preferably, $R_1$ is a substituent independently selected from the group consisting of hydrogen; hydroxy; halogen; and $C_{1-8}$alkanyl;

(3) even more preferably, $R_1$ is a substituent independently selected from the group consisting of hydrogen; hydroxy; methyl; and chloro;

(4) $R_2$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

(5) more preferably $R_2$ is hydrogen or halogen;

(6) even more preferably, $R_2$ is hydrogen or chloro;

(7) $R_3$ is independently selected from the group consisting of hydrogen; hydroxy; fluoro; and chloro;

(8) more preferably $R_3$ is hydrogen;

(9) L is $C_{1-4}$alkandiyl optionally substituted with a substituent selected from the group consisting of $C_{1-8}$alkanyl, $C_{3-8}$cycloalkanyl and phenyl;

(10) more preferably L is $C_{1-4}$alkandiyl optionally substituted with a substituent selected from the group consisting of $C_{3-8}$cycloalkanyl and phenyl;

(11) even more preferably L is —$CH_2$— and —$CH_2CH_2$— optionally substituted with a substituent selected from the group consisting of $C_{3-8}$cycloalkanyl and phenyl;

(12) even more preferably L is —$CH_2$—;

(13) $R_4$ is hydrogen;

(14) $R_5$ is hydrogen;

(15) $R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy; naphthyl optionally substituted with one to three substituents independently selected from the group consisting of $C_{1-8}$alkanyl, chloro, fluoro, $C_{1-8}$alkanyloxy, fluorinated alkanyl, and fluorinated alkanyloxy; and thienyl optionally substituted with one to two substituents selected from the group consisting of $C_{1-8}$alkanyl, chloro, fluoro, $C_{1-8}$alkanyloxy, fluorinated alkanyl, and fluorinated alkanyloxy;

(16) preferably, $R_6$ is phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy;

(17) even more preferably, $R_6$ is phenyl substituted with one to three substituents independently selected from the group consisting of t-butyl, chloro, fluoro, methoxy, trifluoromethyl, and trifluoromethoxy;

(18) Z is O and combinations of (1) through (18), above.

Particularly preferred compounds of Formula (V) are those wherein: X is N; $R_1$ is hydroxy; and $R_3$ is hydrogen. Even more preferred compositions of Formula (V) are those wherein: X is N: $R_1$ is hydroxy; $R_2$, $R_3$, $R_4$, and $R_5$ are hydrogen; $R_6$ is 3,4-di-substituted phenyl, and Z is O.

Other preferred embodiments of the present invention are those in which: (1) $R_1$ is a substituent independently selected from the group consisting of hydrogen; hydroxy; methyl; and chloro; (2) $R_2$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; (3) $R_3$ is independently selected from the group consisting of hydrogen; hydroxy; fluoro; chloro; (4) L is $C_{1-4}$alkandiyl optionally substituted with a substituent selected from the group consisting of $C_{1-8}$alkanyl, $C_{3-8}$cycloalkanyl and phenyl; (5) $R_4$ is hydrogen; (6) $R_5$ is hydrogen; (7) $R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy; naphthyl optionally substituted with one to three substituents independently selected from the group consisting of $C_{1-8}$alkanyl, chloro, fluoro, $C_{1-8}$alkanyloxy, fluorinated alkanyl, and fluorinated alkanyloxy; and thienyl optionally substituted with one to two substituents selected from the group consisting of $C_{1-8}$alkanyl, chloro, fluoro, $C_{1-8}$alkanyloxy, fluorinated alkanyl, and fluorinated alkanyloxy; (8) X is selected from C—H, N and N->O; (9) Y is C—H; (10) Z is O; and (11) any combination of (1) to (10) preceding. Thus, preferred embodiments of the present invention are as described below.

An embodiment of the present invention is directed to compositions comprising a compound of Formula (II) wherein:

$R_1$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

$R_2$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (II) wherein:

$R_1$ is a substituent independently selected from the group consisting of hydrogen; hydroxy; halogen; and $C_{1-8}$alkanyl;

$R_2$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-17}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still another embodiment of the present invention is directed to compositions comprising a compound of Formula (II) wherein:

$R_1$ is a substituent independently selected from the group consisting of hydrogen; hydroxy; methyl; and chloro;

$R_2$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (II) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-18}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_2$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

An embodiment of the present invention is directed to compositions comprising a compound of Formula (II) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_2$ is hydrogen or halogen;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (II) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_2$ is hydrogen or chloro;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still yet another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-17}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; and chloro;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-18}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is hydrogen;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of, morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino; and $C_{1-8}$dialkanylamino;

L is $C_{1-4}$alkandiyl optionally substituted with a substituent selected from the group consisting of $C_{1-8}$alkanyl, $C_{3-8}$cycloalkanyl; and phenyl;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Yet another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkandiyl optionally substituted with a substituent selected from the group consisting of $C_{3-8}$cycloalkanyl and phenyl;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still yet another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-18}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl;

$R_3$ is independently selected from the group consisting of hydrogen; hydroxy; fluoro; chloro; nitro; amino; $C_{1-8}$alkanylamino; and $C_{1-8}$dialkanylamino;

L is —CH$_2$— and —CH$_2$CH$_2$— optionally substituted with a substituent selected from the group consisting of $C_{3-8}$cycloalkanyl and phenyl; preferably, L is —CH$_2$—;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; $diC_{1-7}$alkanylaminocarbonyl; and formyl;

$R_3$ is independently selected from the group consisting of hydrogen; hydroxy; fluoro; chloro; nitro; amino; $C_{1-8}$alkanylamino; and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is hydrogen;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is hydrogen;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy; naphthyl optionally substituted with one to three substituents independently selected from the group consisting of $C_{1-8}$alkanyl, chloro, fluoro, $C_{1-8}$alkanyloxy, fluorinated alkanyl, and fluorinated alkanyloxy; and thienyl optionally substituted with one to two substituents selected from the group consisting of $C_{1-8}$alkanyl, chloro, fluoro, $C_{1-8}$alkanyloxy, fluorinated alkanyl, and fluorinated alkanyloxy;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Yet another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still yet another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is phenyl substituted with one to three substituents independently selected from the group consisting of t-butyl, chloro, fluoro, methoxy, trifluoromethyl, and trifluoromethoxy;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C—H;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (II) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyl; $C_{1-8}$alkanylthio optionally substituted with one or substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

z is O; and enantiomers, diastereomers, tautomers, solvates, and pharmaceutically acceptable salts thereof.

An embodiment of the present invention is directed to compositions comprising a compound of Formula (III) wherein:

$R_2$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (III) wherein:

$R_2$ is one to three substituents independently selected from the group consisting of hydrogen and halogen;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (III) wherein:

$R_2$ is one to three substituent independently selected from the group consisting of hydrogen and chloro;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkandiyl optionally substituted with a substituent selected from the group consisting of $C_{1-8}$alkanyl, $C_{3-8}$cycloalkanyl and phenyl;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Yet another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkandiyl optionally substituted with a substituent selected from the group consisting of $C_{3-8}$cycloalkanyl and phenyl;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still yet another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is —CH$_2$— and —CH$_2$CH$_2$— optionally substituted with a substituent selected from the group consisting of $C_{3-8}$cycloalkanyl and phenyl; preferably, L is —CH$_2$—;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is hydrogen;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$ alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is hydrogen;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy; naphthyl optionally substituted with one to three substituents independently selected from the group consisting of $C_{1-8}$alkanyl, chloro, fluoro, $C_{1-8}$alkanyloxy, fluorinated alkanyl, and fluorinated alkanyloxy; and thienyl optionally substituted with one to two substituents selected from the group consisting of $C_{1-8}$alkanyl, chloro, fluoro, $C_{1-8}$alkanyloxy, fluorinated alkanyl, and fluorinated alkanyloxy;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Yet another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is phenyl substituted with one to three substituents independently selected from the group consisting of $C_{1-8}$alkanyl, chloro, fluoro, $C_{1-18}$alkanyloxy, fluorinated alkanyl, and fluorinated alkanyloxy;

X is selected from C—H, N and N->O;
Y is C or N, provided that if Y is N then $R_3$ is absent;
Z is selected from the group consisting of O and S; and enantiomers, diastereomers, tautomers, solvates, and pharmaceutically acceptable salts thereof.

Still yet another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is phenyl substituted with one to three substituents independently selected from the group consisting of t-butyl, chloro, fluoro, methoxy, trifluoromethyl, and trifluoromethoxy;

X is selected from C—H, N and N->O;
Y is C or N, provided that if Y is N then $R_3$ is absent;
Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C—H;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (III) wherein:

$R_2$ is one to three substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

z is O; and enantiomers, diastereomers, tautomers, solvates, and pharmaceutically acceptable salts thereof.

An embodiment of the present invention is directed to compositions comprising a compound of Formula (IV) wherein:

$R_1$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

$R_2$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (IV) wherein:

$R_1$ is a substituent independently selected from the group consisting of hydrogen; hydroxy; halogen; and $C_{1-8}$alkanyl;

$R_2$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-18}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still another embodiment of the present invention is directed to compositions comprising a compound of Formula (IV) wherein:

$R_1$ is a substituent independently selected from the group consisting of hydrogen; hydroxy; methyl; and chloro;

$R_2$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (IV) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_2$ is a substituent independently selected from the group consisting of hydrogen; hydroxy; halogen; and $C_{1-8}$alkanyl optionally substituted with one or more substituents independently selected from the group consisting of halogen, fluorinated alkanyl and $C_{1-8}$alkanyloxy;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano, naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

An embodiment of the present invention is directed to compositions comprising a compound of Formula (IV) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_2$ is a substituent independently selected from the group consisting of hydrogen and halogen;

$R_3$ is independently selected from the group consisting of hydrogen; hydroxy; fluoro; chloro; nitro; amino; $C_{1-8}$alkanylamino; and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (IV) wherein:

$R_1$ is a substituent independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_2$ is a substituent independently selected from the group consisting of hydrogen and chloro;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still yet another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; and chloro;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is hydrogen;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-18}$dialkanylamino;

L is $C_{1-4}$alkandiyl optionally substituted with a substituent selected from the group consisting of $C_{1-8}$alkanyl, $C_{3-8}$cycloalkanyl and phenyl;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Yet another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-17}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkandiyl optionally substituted with a substituent selected from the group consisting of $C_{3-8}$cycloalkanyl and phenyl;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still yet another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is —CH$_2$— and —CH$_2$CH$_2$— optionally substituted with a substituent selected from the group consisting of $C_{3-8}$cycloalkanyl and phenyl; preferably, L is —CH$_2$—;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of, $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is hydrogen;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;
Y is C or N, provided that if Y is N then $R_3$ is absent;
Z is selected from the group consisting of O and S; and enantiomers, diastereomers, tautomers, solvates, and pharmaceutically acceptable salts thereof.

Another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is hydrogen;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;
Y is C or N, provided that if Y is N then $R_3$ is absent;
Z is selected from the group consisting of O and S; and enantiomers, diastereomers, tautomers, solvates, and pharmaceutically acceptable salts thereof.

Another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy; naphthyl optionally substituted with one to three substituents independently selected from the group consisting of $C_{1-8}$alkanyl, chloro, fluoro, $C_{1-8}$alkanyloxy, fluorinated alkanyl, and fluorinated alkanyloxy; and thienyl optionally substituted with one to two substituents selected from the group consisting of $C_{1-8}$alkanyl, chloro, fluoro, $C_{1-8}$alkanyloxy, fluorinated alkanyl, and fluorinated alkanyloxy;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Yet another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is phenyl substituted with one to three substituents independently selected from the group consisting of $C_{1-8}$alkanyl, chloro, fluoro, $C_{1-8}$alkanyloxy, fluorinated alkanyl, and fluorinated alkanyloxy;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Still yet another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is phenyl substituted with one to three substituents independently selected from the group consisting of t-butyl, chloro, fluoro, methoxy, trifluoromethyl, and trifluoromethoxy;

X is selected from C—H, N and N->O;

Y is C or N, provided that if Y is N then $R_3$ is absent;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C—H;

Z is selected from the group consisting of O and S; and enantiomers, diastereomers, tautomers, solvates, and pharmaceutically acceptable salts thereof.

Furthermore, another embodiment of the present invention is directed to compositions comprising a compound of Formula (IV) wherein:

$R_1$ and $R_2$ are substituents independently selected from the group consisting of hydrogen; hydroxy; halogen; $C_{1-8}$alkanyl optionally substituted with one or more substituents independently selected from the group consisting of halogen, fluorinated alkanyl and $C_{1-8}$alkanyloxy; $C_{1-8}$alkanyloxy optionally substituted with one or more substituents independently selected from the group consisting of halogen, fluorinated alkanyl and $C_{1-8}$alkanyloxy; fluorinated alkanyloxy; fluorinated alkanyl; $C_{1-8}$alkanylthio optionally substituted with one or more substituents independently selected from the group consisting of halogen, fluorinated alkanyl and $C_{1-8}$alkanyloxy; $C_{3-8}$cycloalkanyl; $C_{3-8}$cycloalkanyloxy; nitro; amino; $C_{1-8}$alkanylamino; $C_{1-8}$dialkanylamino; $C_{3-8}$cycloalkanylamino; cyano; carboxy; $C_{1-7}$alkanyloxycarbonyl; $C_{1-7}$alkanylcarbonyloxy; $C_{1-7}$alkanylaminocarbonyl; $C_{1-7}$alkanylcarbonylamino; di$C_{1-7}$alkanylaminocarbonyl; and formyl;

$R_3$ is independently selected from the group consisting of hydrogen; hydroxy; fluoro; chloro; nitro; amino; $C_{1-8}$alkanylamino, and $C_{1-8}$dialkanylamino;

L is $C_{1-4}$alkyldiyl optionally substituted with a substituent selected from the group consisting of $C_{1-8}$alkanyl, $C_{3-8}$cycloalkanyl and phenyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, amino, di($C_{1-3}$)alkanylamino, and $C_{1-3}$alkanylamino;

$R_4$ is selected from the group consisting of hydrogen and $C_{1-3}$alkanyl;

$R_5$ is selected from the group consisting of hydrogen and $C_{1-3}$alkanyl;

$R_6$ is selected from the group consisting of phenyl substituted with one to three substituents independently selected from the group consisting of $C_{1-8}$alkanyl, $C_{3-8}$cycloalkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; naphthyl optionally substituted with one to three substituents independently selected from the group consisting of $C_{1-8}$alkanyl, halogen, $C_{1-8}$alkanyloxy, hydroxy, fluorinated alkanyl, fluorinated alkanyloxy, nitro, amino, di($C_{1-8}$)alkanylamino, $C_{1-8}$alkanylamino, aminosulfonyl, $C_{1-8}$alkanylaminosulfonyl, di($C_{1-8}$)alkanylaminosulfonyl and cyano; heteroaryl optionally substituted with one to two substituents selected from the group consisting of $C_{1-8}$alkanyl, halogen, $C_{1-8}$alkanyloxy, hydroxy, fluorinated alkanyl, and fluorinated alkanyloxy wherein said heteroaryl is thienyl, furanyl, benzthienyl, benzfuranyl, pyridyl, or benzimidazole; $C_{5-7}$cycloalkanyl optionally substituted with $C_{1-6}$alkanyl; and cyclic heteroalkanyl selected from the group consisting of morpholinyl, piperazinyl, piperidinyl, imidazolidinyl, pyrazolidinyl, thiomorpholinyl, and pyrrolidinyl;

X is selected from C—H, N and N->O;

Y is C or N, provided that if Y is N then $R_3$ is absent;

Z is O; and enantiomers, diastereomers, tautomers, solvates, and pharmaceutically acceptable salts thereof.

Another embodiment of the present invention is directed to compositions comprising a compound of Formula (Ia) or (V), the compound selected from the group consisting of:

a compound of formula (Ia) wherein $R_1$ is H, $R_2$ is H, $R_3$ is H, $R_4$ is H, $R_5$ is H, L is —$CH_2CH_2$—, $R_6$ is (3,4-diCl)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (3-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-Cl)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (3,4-diCl)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-Cl)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (3-$CF_3$)Ph, X is N, and Y is C;

a compound of formula (Ia) wherein $R_1$ is Me, $R_2$ is H, $R_3$ is H, $R_4$ is H, $R_5$ is H, L is —$CH_2$—, $R_6$ is (3,4-diCl)Ph, X is N, and Y is C;

a compound of formula (Ia) wherein $R_1$ is Me, $R_2$ is H, $R_3$ is H, $R_4$ is H, $R_5$ is H, L is —$CH_2$—, $R_6$ is (3-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2CH((4\text{-}OMe)Ph)$-, $R_6$ is Pyridin-3-yl, X is N, and Y is C;

a compound of formula (Ia) wherein $R_1$ is H, $R_2$ is H, $R_3$ is H, $R_4$ is H, $R_5$ is H, L is —$CH_2CH(-CH_2Ph)$-, $R_6$ is (4-OMe)Ph, X is N, and Y is C;

a compound of formula (Ia) wherein $R_1$ is H, $R_2$ is H, $R_3$ is H, $R_4$ is H, $R_5$ is H, L is —$CH_2CH(-CH_2\text{cyclohexyl})$-, $R_6$ is (4-OMe)Ph, X is N, and Y is C;

a compound of formula (Ia) wherein $R_1$ is OH, $R_2$ is H, $R_3$ is H, $R_4$ is H, $R_5$ is H, L is —$CH_2$—, $R_6$ is (4-t-Bu)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (4-Cl)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is Pyridin-3-yl, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (4-$OCF_3$)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (4-$CF_3$)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$)Ph, X is C and Y is C;

a compound of formula (Ia) wherein $R_1$ is H, $R_2$ is H, $R_3$ is H, $R_4$ is H, $R_5$ is H, L is —$CH_2$—, $R_6$ is (3-$CF_3$-4-Cl)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-OMe)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-$OCF_3$)Ph, X is N, and Y is C;

a compound of formula (Ia) wherein $R_1$ is OH, $R_2$ is H, $R_3$ is H, $R_4$ is H, $R_5$ is H, L is —$CH_2CH_2$—, $R_6$ is Ph, X is C and Y is C;

a compound of formula (Ia) wherein $R_1$ is OH, $R_2$ is H, $R_3$ is H, $R_4$ is H, $R_5$ is Et, L is —$CH_2$—, $R_6$ is Ph, X is C and Y is C;

a compound of formula (Ia) wherein $R_1$ is OH, $R_2$ is H, $R_3$ is H, $R_4$ is H, $R_5$ is Benzyl, L is —$CH_2$—, $R_6$ is Ph, X is C and Y is C;

a compound of formula (Ia) wherein $R_1$ is OH, $R_2$ is H, $R_3$ is H, $R_4$ is H, $R_5$ is Me, L is —$CH_2$—, $R_6$ is Ph, X is C and Y is C;

a compound of formula (Ia) wherein $R_1$ is OH, $R_2$ is H, $R_3$ is H, $R_4$ is H, $R_5$ is H, L is —$CH_2CH_2$—, $R_6$ is (3,4-diCl)Ph, X is C and Y is C;

a compound of formula (Ia) wherein $R_1$ is OH, $R_2$ is H, $R_3$ is H, $R_4$ is H, $R_5$ is —$CH_2CH_2$PH, L is —$CH_2$—, $R_6$ is Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (6-$CF_3$)Pyridin-3-yl, X is C and Y is C;

a compound of formula (Ia) wherein $R_1$ is OH, $R_2$ is H, $R_3$ is H, $R_4$ is H, $R_5$ is Me, L is —$CH_2$—, $R_6$ is (3,4-diCl)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (3,4-diCl)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is Benzimidazol-2-yl, X is C and Y is C;

a compound of formula (Ia) wherein $R_1$ is H, $R_2$ is H, $R_3$ is H, $R_4$ is H, $R_5$ is H, L is —$CH_2$—, $R_6$ is (4-t-Bu)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-t-Bu)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-OMe)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-$OCF_3$)Ph, X is N, and Y is C;

a compound of formula (Ia) wherein $R_1$ is OH, $R_2$ is H, $R_3$ is H, $R_4$ is H, $R_5$ is H, L is —$CH_2$—, $R_6$ is (5-thiophen-2-yl)Thiophen-2-yl, X is C and Y is C;

a compound of formula (Ia) wherein $R_1$ is OH, $R_2$ is H, $R_3$ is H, $R_4$ is H, $R_5$ is H, L is —$CH_2$—, $R_6$ is Benzthiophen-2-yl, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (2-Br)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (3,4-diF)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (5-Cl)Benzthiophen-3-yl, X is C and Y is C;

a compound of formula (Ia) wherein $R_1$ is OH, $R_2$ is H, $R_3$ is H, $R_4$ is H, $R_5$ is H, L is —$CH_2CH_2$—, $R_6$ is (2-Cl)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (2,6-diCl)Ph, X is C and Y is C;

a compound of formula (Ia) wherein $R_1$ is OH, $R_2$ is H, $R_3$ is H, $R_4$ is H, $R_5$ is H, L is —$CH_2CH_2$—, $R_6$ is (4-$SO_2NH_2$)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (2,4-diCl)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (5-Pyridin-2-yl)Thiophene-2-yl, X is C and Y is C;

a compound of formula (Ia) wherein $R_1$ is OH, $R_2$ is H, $R_3$ is H, $R_4$ is H, $R_5$ is H, L is —$CH_2$—, $R_6$ is Pyridin-2-yl, X is C and Y is C;

a compound of formula (Ia) wherein $R_1$ is OH, $R_2$ is H, $R_3$ is H, $R_4$ is H, $R_5$ is H, L is —$CH_2CH(Ph)$-, $R_6$ is Ph, X is C and Y is C;

a compound of formula (Ia) wherein $R_1$ is OH, $R_2$ is H, $R_3$ is H, $R_4$ is H, $R_5$ is H, L is —$CH_2CH_2CH_2$—, $R_6$ is Morpholin-1-yl, X is C and Y is C;

a compound of formula (Ia) wherein $R_1$ is OH, $R_2$ is H, $R_3$ is H, $R_4$ is H, $R_5$ is H, L is —$CH_2$—, $R_6$ is 6,6-DiMethyl-bicyclo[3.1.1]heptan-2-yl, X is C and Y is C;

a compound of formula (Ia) wherein $R_1$ is OH, $R_2$ is H, $R_3$ is H, $R_4$ is H, $R_5$ is H, L is —$CH_2$—, $R_6$ is Cyclohexyl, X is C and Y is C;

a compound of formula (Ia) wherein $R_1$ is OH, $R_2$ is H, $R_3$ is H, $R_4$ is H, $R_5$ is H, L is —$CH_2CH_2$—, $R_6$ is Pyridin-2-yl, X is C and Y is C;

a compound of formula (Ia) wherein $R_1$ is H, $R_2$ is $C_1$, $R_3$ is H, $R_4$ is H, $R_5$ is H, L is —$CH_2$—, $R_6$ is (4-$CF_3$)Ph, X is N, and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$-4-F)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$-4-Cl)Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (3,5-di$CF_3$)Ph, X is C and Y is C;

a compound of formula (Ia) wherein $R_1$ is H, $R_2$ is H, $R_3$ is $C_1$, $R_4$ is H, $R_5$ is H, L is —$CH_2$—, $R_6$ is (4-$CF_3$)Ph, X is N, and Y is C;

a compound of formula (Ia) wherein $R_1$ is OH, $R_2$ is H, $R_3$ is H, $R_4$ is H, $R_5$ is H, L is —CH(Me)—, $R_6$ is (3-$CF_3$-4-Cl)Ph, X is C and Y is C;

a compound of formula (Ia) wherein $R_1$ is OH, $R_2$ is H, $R_3$ is H, $R_4$ is H, $R_5$ is H, L is —CH(Ph)$CH_2$—, $R_6$ is Ph, X is C and Y is C;

a compound of formula (Ia) wherein $R_1$ is OH, $R_2$ is H, $R_3$ is H, $R_4$ is H, $R_5$ is H, L is —$CH_2$—, $R_6$ is (2,4-diCl)Ph, X is C and Y is C; and a compound of formula (V) wherein $R_1$ is OH, $R_2$ is H, $R_3$ is H, $R_4$ is H, $R_5$ is H, L is —$CH_2$—, $R_6$ is (3-$CF_3$,4-Cl)Ph, X is N, and Y is C.

Preferred compounds of Formula (Ia) or (V) are selected from the group consisting of:

a compound of formula (Ia) wherein $R_1$ is OH, $R_2$ is H, $R_3$ is H, $R_4$ is H, $R_5$ is H, L is —$CH_2$—, $R_6$ is (4-$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-$OCF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-t-Bu)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$-4-Cl)Ph, X is C, and Y is C;

a compound of formula (Ia) wherein $R_1$ is OH, $R_2$ is H, $R_3$ is H, $R_4$ is H, $R_5$ is H, L is —$CH_2CH_2$—, $R_6$ is (3,4-diCl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3,4-diCl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (2,4-diCl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-Cl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3,5-di$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3,4-diF)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (6-$CF_3$)Pyridin-3-yl, X is C, and Y is C;

a compound of formula (Ia) wherein $R_1$ is OH, $R_2$ is H, $R_3$ is H, $R_4$ is H, $R_5$ is H, L is —$CH_2CH_2$—, $R_6$ is Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is Ph, X is C, and Y is C;

a compound of formula (Ia) wherein $R_1$ is H, $R_2$ is H, $R_3$ is H, $R_4$ is H, $R_5$ is H, L is —$CH_2$—, $R_6$ is (4-t-Bu)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (3-$CF_3$-4-Cl)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-$OCF_3$)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-t-Bu)Ph, X is N, and Y is C;

a compound of formula (Ia) wherein $R_1$ is H, $R_2$ is H, $R_3$ is H, $R_4$ is H, $R_5$ is H, L is —$CH_2$CH(—$CH_2$cyclohexyl)-, $R_6$ is (4-OMe)Ph, X is N, and Y is C;

a compound of formula (Ia) wherein $R_1$ is H, $R_2$ is H, $R_3$ is H, $R_4$ is H, $R_5$ is H, L is —$CH_2$CH(—$CH_2$Ph)-, $R_6$ is (4-OMe)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-$OCF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-$CF_3$)Ph, X is N, and Y is C;

a compound of formula (Ia) wherein $R_1$ is H, $R_2$ is $C_1$, $R_3$ is H, $R_4$ is H, $R_5$ is H, L is —$CH_2$—, $R_6$ is (4-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (3,4-diCl)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (3,4-diCl)Ph, X is N, and Y is C;

a compound of formula (Ia) wherein $R_1$ is Me, $R_2$ is H, $R_3$ is H, $R_4$ is H, $R_5$ is H, L is —$CH_2$—, $R_6$ is (3,4-diCl)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (3-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-Cl)Ph, X is N, and Y is C;

a compound of formula (Ia) wherein $R_1$ is Me, $R_2$ is H, $R_3$ is H, $R_4$ is H, $R_5$ is H, L is —$CH_2$—, $R_6$ is (3-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (3-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-Cl)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-OMe)Ph, X is N, and Y is C; and a compound of formula (V) wherein $R_1$ is OH, $R_2$ is H, $R_3$ is H, $R_4$ is H, $R_5$ is H, L is —$CH_2$—, $R_6$ is (3-$CF_3$,4-Cl)Ph, X is N, and Y is C.

More preferred compounds of Formula (Ia) or (V) are selected from the group consisting of:

a compound of formula (Ia) wherein $R_1$ is OH, $R_2$ is H, $R_3$ is H, $R_4$ is H, $R_5$ is H, L is —$CH_2$—, $R_6$ is (4-$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-$OCF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-t-Bu)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$-4-Cl)Ph, X is C, and Y is C;

a compound of formula (Ia) wherein $R_1$ is OH, $R_2$ is H, $R_3$ is H, $R_4$ is H, $R_5$ is H, L is —$CH_2CH_2$—, $R_6$ is (3,4-diCl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3,4-diCl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (2,4-diCl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-Cl)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3,5-di$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3,4-diF)Ph, X is C, and Y is C;

a compound of formula (Ia) wherein $R_1$ is H, $R_2$ is H, $R_3$ H, $R_4$ is H, $R_5$ is H, L is —$CH_2$—, $R_6$ is (4-t-Bu)Ph, X is N, and Y is C;

a compound of formula (Ia) wherein $R_1$ is H, $R_2$ is H, $R_3$ H, $R_4$ is H, $R_5$ is H, L is —$CH_2$—, $R_6$ is (3-$CF_3$-4-Cl)Ph, X is N, and Y is C;

a compound of formula (Ia) wherein $R_1$ is H, $R_2$ is H, $R_3$ H, $R_4$ is H, $R_5$ is H, L is —$CH_2$—, $R_6$ is (4-$OCF_3$)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-t-Bu)Ph, X is N, and Y is C;

a compound of formula (Ia) wherein $R_1$ is H, $R_2$ is H, $R_3$ is H, $R_4$ is H, $R_5$ is H, L is —$CH_2CH$(—$CH_2$cyclohexyl)-, $R_6$ is (4-OMe)Ph, X is N, and Y is C;

a compound of formula (Ia) wherein $R_1$ is H, $R_2$ is H, $R_3$ is H, $R_4$ is H, $R_5$ is H, L is —$CH_2CH$(—$CH_2$Ph)-, $R_6$ is (4-OMe)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-$OCF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-$CF_3$)Ph, X is N, and Y is C;

a compound of formula (Ia) wherein $R_1$ is H, $R_2$ is $C_1$, $R_3$ is H, $R_4$ is H, $R_5$ is H, L is —$CH_2$—, $R_6$ is (4-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (3,4-diCl)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (3,4-diCl)Ph, X is N, and Y is C;

a compound of formula (Ia) wherein $R_1$ is Me, $R_2$ is H, $R_3$ is H, $R_4$ is H, $R_5$ is H, L is —$CH_2$—, $R_6$ is (3,4-diCl)Ph, X is N, and Y is C; and a compound of formula (V) wherein $R_1$ is OH, $R_2$ is H, $R_3$ is H, $R_4$ is H, $R_5$ is H, L is —$CH_2$—, $R_6$ is (3-$CF_3$,4-Cl)Ph, X is N, and Y is C.

Still other more preferred compounds of Formula (Ia) or (V) are selected from the group consisting of:

a compound of formula (Ia) wherein $R_1$ is OH, $R_2$ is H, $R_3$ is H, $R_4$ is H, $R_5$ is H, L is —$CH_2$—, $R_6$ is (4-$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-$OCF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (4-t-Bu)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$)Ph, X is C, and Y is C;

a compound of formula (Ia) wherein $R_1$ is OH, $R_2$ is H, $R_3$ is H, $R_4$ is H, $R_5$ is H, L is —$CH_2$—, $R_6$ is (3-$CF_3$-4-Cl)Ph, X is C, and Y is C;

a compound of formula (Ia) wherein $R_1$ is OH, $R_2$ is H, $R_3$ is H, $R_4$ is H, $R_5$ is H, L is —$CH_2CH_2$—, $R_6$ is (3,4-diCl)Ph, X is C, and Y is C;

a compound of formula (Ia) wherein $R_1$ is H, $R_2$ is H, $R_3$ is H, $R_4$ is H, $R_5$ is H, L is —$CH_2$—, $R_6$ is (4-t-Bu)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-$CF_3$)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (3-$CF_3$-4-Cl)Ph, X is N, and Y is C;

a compound of formula (Ia) wherein $R_1$ is H, $R_2$ is H, $R_3$ is H, $R_4$ is H, $R_5$ is H, L is —$CH_2$—, $R_6$ is (4-$OCF_3$)Ph, X is N, and Y is C;

a compound of formula (Ia) wherein $R_1$ is H, $R_2$ is H, $R_3$ is H, $R_4$ is H, $R_5$ is H, L is —$CH_2CH_2$—, $R_6$ is (4-t-Bu)Ph, X is N, and Y is C; and a compound of formula (V) wherein $R_1$ is OH, $R_2$ is H, $R_3$ is H, $R_4$ is H, $R_5$ is H, L is —$CH_2$—, $R_6$ is (3-$CF_3$,4-Cl)Ph, X is N, and Y is C.

Another embodiment of the present invention is directed to compositions comprising a compound of Formula (II), the compound selected from the group consisting of:

a compound of formula (II) wherein $R_1$ is H, $R_2$ is H, $R_4$ is H, $R_5$ is H, L is $R_6$ is (3-$CF_3$)Ph, and Z is O;

a compound of formula (II) wherein $R_1$ is H, $R_2$ is H, $R_4$ is H, $R_5$ is H, L is —$CH_2$—, $R_6$ is (4-$CF_3$)Ph, and Z is O;

a compound of formula (II) wherein $R_1$ is H, $R_2$ is H, $R_4$ is H, $R_5$ is H, L is —$CH_2$—, $R_6$ is (3,4-diCl)Ph, and Z is O;

a compound of formula (II) wherein $R_1$ is H, $R_2$ is H, $R_4$ is H, $R_5$ is H, L is —$CH_2CH_2$—, $R_6$ is (3,4-diCl)Ph, and Z is O;

a compound of formula (II) wherein $R_1$ is H, $R_2$ is H, $R_4$ is H, $R_5$ is H, L is —$CH_2$—, $R_6$ is (4-N(Me)$_n$-pentyl)Ph, and Z is O; and a compound of formula (II) wherein $R_1$ is H, $R_2$ is H, $R_4$ is H, $R_5$ is H, L is —$CH_2$—, $R_6$ is (4-N(Me)$CH_2$cyclohexyl)Ph, and Z is O.

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201–217; *J. Pharm. Sci.*, 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexane-sulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formulae (I), (II), (III), (IV) and (V)(I), (II), (III), (IV), and (V) and (V) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

A therapeutically effective amount for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as vanilloid receptor modulators is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

As modulators of the vanilloid VR1 ion channel, the compounds of Formulae (I), (II), (III), (IV), and (V), and (V) are useful in methods for treating or preventing a disease or condition in a mammal which disease or condition is affected by the modulation of one or more vanilloid receptors. Such methods comprises administering to a mammal in need of such treatment or prevention a therapeutically effective amount of a compound, salt or solvate of Formulae (I), (II), (III), (IV), and (V). In particular, the compounds of Formulae (I), (II), (III), (IV), and (V) are useful for in methods for preventing or treating a chronic- or acute-pain causing diseases or conditions and pulmonary dysfunction, and more particulalry, in treating diseases or conditions that cause inflammatory pain, burning pain, itch or urinary incontinence, and chronic obstructive pulmonary disease.

By way of example only, the compounds of Formulae (I), (II), (III), (IV), and (V) are useful for treating diseases and conditions selected from the group consisting of osteoarthritis, rheumatoid arthritis, fibromyalgia, migraine, headache, toothache, burn, sunburn, snake bite (in particular, venomous snake bite), spider bite, insect sting, neurogenic bladder, benign prostatic hypertrophy, interstitial cystitis, urinary tract infection, cough, asthma, chronic obstructive pulmonary disease, rhinitis, contact dermatitis/hypersensitivity, itch, eczema, anxiety, panic disorders, pharyngitis, mucositis, enteritis, cellulites, peripheral neuropathy, bilateral peripheral neuropathy, diabetic neuropathy, postherpetic neuralgia, trigeminal neuralgia, causalgia, sciatic neuritis, mandibular joint neuralgia, peripheral neuritis, polyneuritis, stump pain, phantom limb pain, bony fractures, post-operative ileus, irritable bowel syndrome, inflammatory bowel diseases such as Crohn's Disease and ulcerative colitis, cholecystitis, pancreatitis, postmastectomy pain syndrome, oral neuropathic pain, Charcot's pain, reflex sympathetic dystrophy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, intestinal gas, menstruation, hot flash, cancer, and trauma.

While the present invention comprises compositions comprising one or more of the compounds of Formulae (I), (II), (III), (IV), and (V), the present invention also comprises compositoins comprising intermediates used in the manufacture of compounds of Formulae (I), (II), (III), (IV), and (V).

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

The ureas of formulae (I), (II), (III), (IV) and (V) that comprise this invention are synthesized using several distinct chemical methods. An aminoheterocycle [(Ia-b); X or Y=N] such as a chlorinated aminoisoquinoline, aminoisoquinoline, or aminoquinoline, or an arylamine such as an aminonaphthol [(Ia): X=CH; Y=C—$R_3$], is reacted with a chloroformate, such as phenyl chloroformate in an inert solvent, with or without added base, to afford the corresponding phenylcarbamates. Separately these carbamates are reacted with an amine ($R_5$NH-L-$R_6$ or $H_2$N-L-$R_6$), such as a benzylamine or phenethylamine, in a polar solvent such as dimethylsulfoxide, with or without added base, from room temperature to approximately 150 C, to produce the urea compounds of this invention [Formula (I)) (Scheme 1) and Formula (II) (Scheme 2)] in which Z=O. The use of chlorothionoformates in place of chloroformates produces the analogous thioureas (Z=S).

SCHEME 1

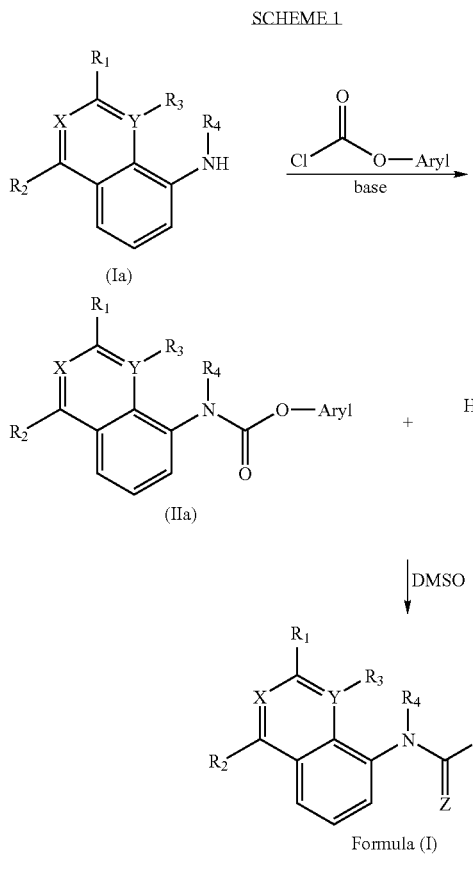

SCHEME 2

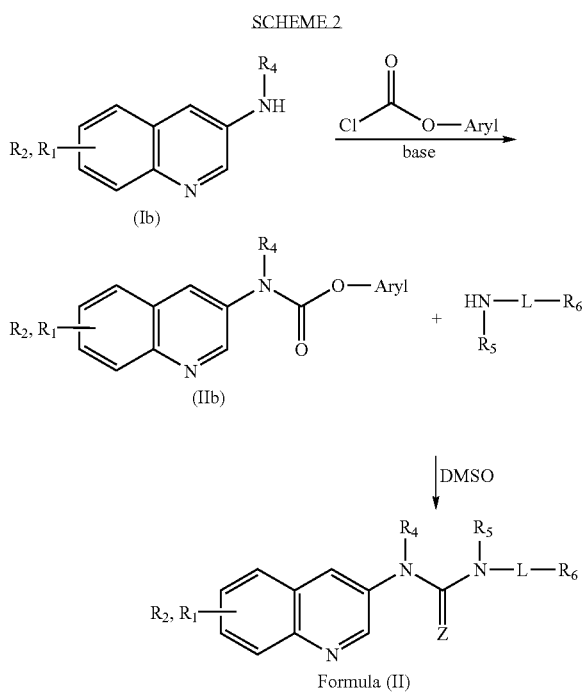

Alternatively, an aminoheterocycle [(Ia-b); X or Y=N] such as a chlorinated aminoisoquinoline, aminoisoquinoline, or aminoquinoline, or an arylamine such as aminonaphthol [(Ia): X=CH; Y=C—$R_3$], is reacted with isocyanato- or isothiocyanato-benzylamine or phenethylamine in the presence of a base to produce urea compounds of this invention wherein $R_5$=H (Schemes 3–4). Benzylamines may be reacted with phosgene or thiophosgene (or suitable equivalents thereof), in the presence of a base, such as an organic amine, to produce the corresponding isocyanate (Z=O) and thiocyanate (Z=S) reagents. In examples wherein the arylamine is an aminonaphthol, protecting group manipulations may be used to mask and subsequently liberate the phenolic OH group and this practice is well known to those skilled in the art.

SCHEME 3

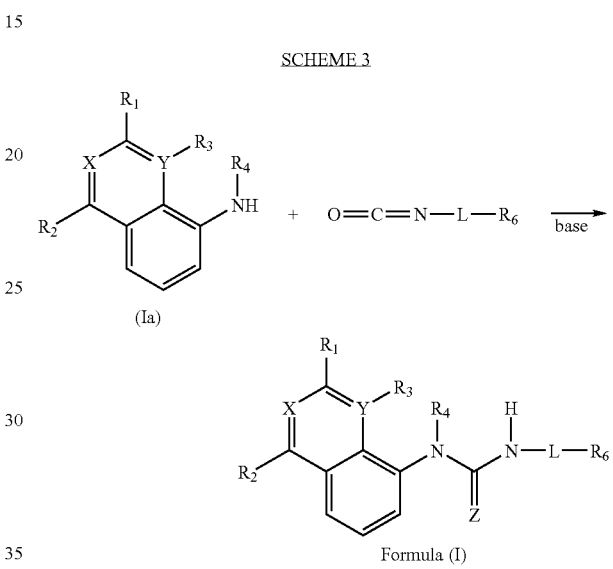

SCHEME 4

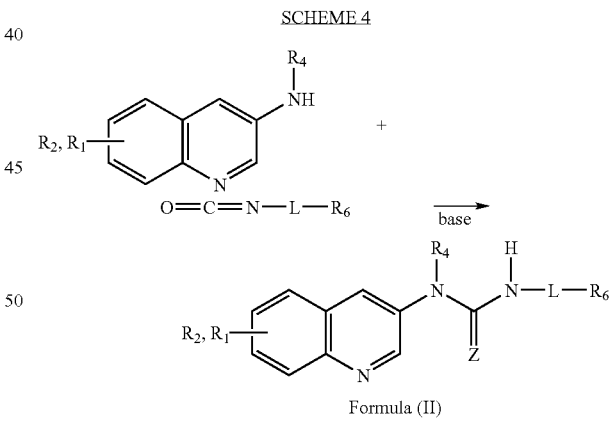

The ureas of formula (IV) are synthesized using several chemical methods. An appropriately substituted aminoisoquinoline (Ia) is reacted with a chloroformate, such as phenyl chloroformate in an inert solvent, with or without added base, to afford the corresponding phenylcarbamates. Separately these carbamates are reacted with an amine ($R_5$NH-L-$R_6$ or $H_2$N-L-$R_6$), such as a benzylamine or phenethylamine, in a polar solvent such as dimethylsulfoxide, with or without added base, from room temperature to approximately 150 C, to produce the urea compounds of this invention [Formula (IV)) (Scheme X)] in which Z=O. The use of chlorothionoformates in place of chloroformates produces the analogous thioureas (Z=S).

SCHEME 5

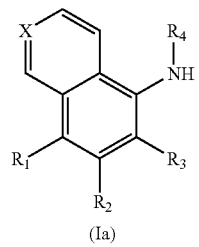
(Ia)

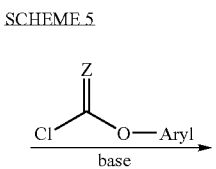

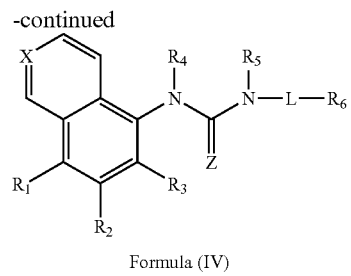
Formula (IV)

Appropriately substituted aminoisoquinolines to be used in the synthesis of ureas of formula (IV) may be obtained by several synthetic routes as described below.

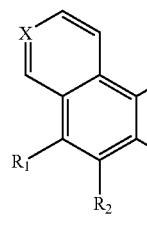
(IIa)

+ 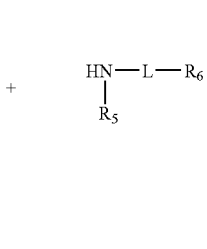

↓ DMSO

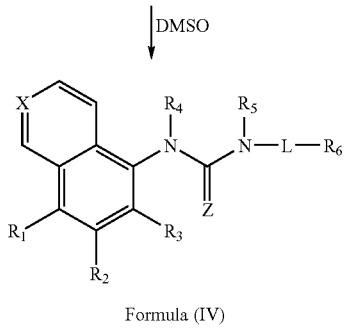
Formula (IV)

SCHEME 7

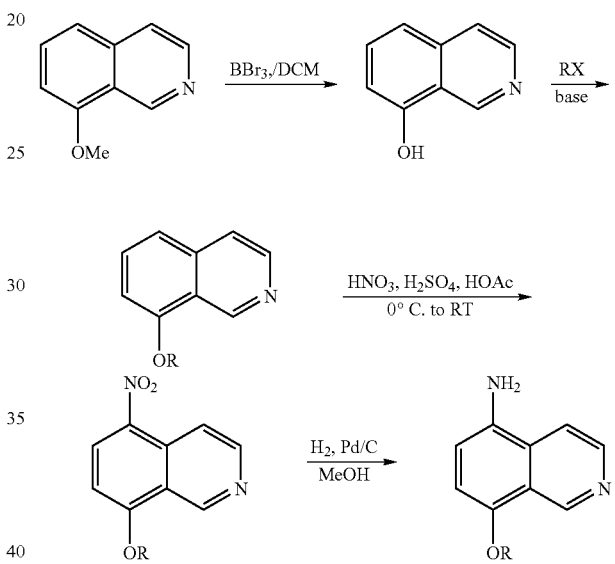

Alternatively, an appropriately substituted aminoisoquinoline, [(Ia)] is reacted with isocyanato- or isothiocyanato-benzylamine or phenethylamine in the presence of a base to produce urea compounds of this invention wherein $R_5$=H (Scheme 6). Benzylamines may be reacted with phosgene or thiophosgene (or suitable equivalents thereof), in the presence of a base, such as an organic amine, to produce the corresponding isocyanate (Z=O) and thiocyanate (Z=S) reagents.

In Scheme 7, 8-methoxyisoquinoline is prepared by modification of the method of Yoshida et al., *Bioorg. Med. Chem.* 1999, 7, 2647. Demethylation is accomplished by reaction with boron tribromide in dichloromethane at reflux temperature to give the 8-hydroxyisoquinoline. This may be reacted with a suitable alkylating agent in the presence of base. Nitration may then be achieved by reaction of the isoquinoline with a nitrating agent such as potassium nitrate in sulfuric acid or a mixture of nitric acid, sulfuric acid and acetic acid. The nitro intermediate may then be reduced to the amino isoquinoline ester by hydrogenation with a suitable catalyst or another suitable reducing agent such as tin(II) chloride. This amino isoquinoline may then be reacted as described in Schemes 5 and 6 to give the target ureas.

SCHEME 6

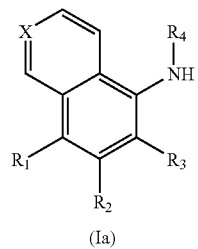 + 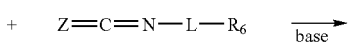

SCHEME 8

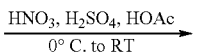

HNO$_3$, H$_2$SO$_4$, HOAc
0° C. to RT

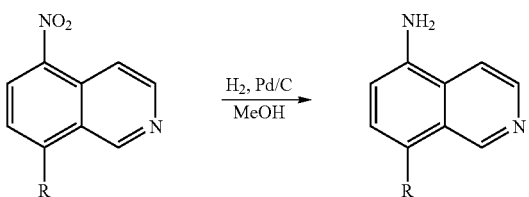

In Scheme 8, an 8-alkylisoquinoline may be prepared by modification of the method of Yoshida et al., *Bioorg. Med. Chem.* 1999, 7, 2647. Nitration may then be achieved by reaction of the isoquinoline with a nitrating agent such as potassium nitrate in sulfuric acid or a mixture of nitric acid, sulfuric acid and acetic acid. The nitro intermediate may then be reduced to the amino isoquinoline ester by hydrogenation with a suitable catalyst or another suitable reducing agent such as tin(II) chloride. This amino isoquinoline may then be reacted as described in Schemes 5 and 6 to give the target ureas.

sium nitrate in sulfuric acid or a mixture of nitric acid, sulfuric acid and acetic acid. The resulting nitro compound is oxidized with chromate in sulfuric acid to give the acid, which is not isolated but immediately reacted with methanol at reflux to give the ester. The nitro ester is then reduced by hydrogenation with a suitable catalyst or another suitable reducing agent such as tin(II) chloride to the amino isoquinoline ester. This amino isoquinoline may then be reacted as described in Schemes 5 and 6 to give the target ureas. Further, the ester may be hydrolyzed to the acid and then reacted as stated above to give target compounds.

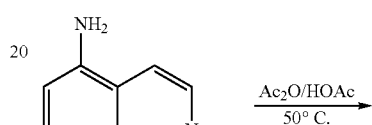

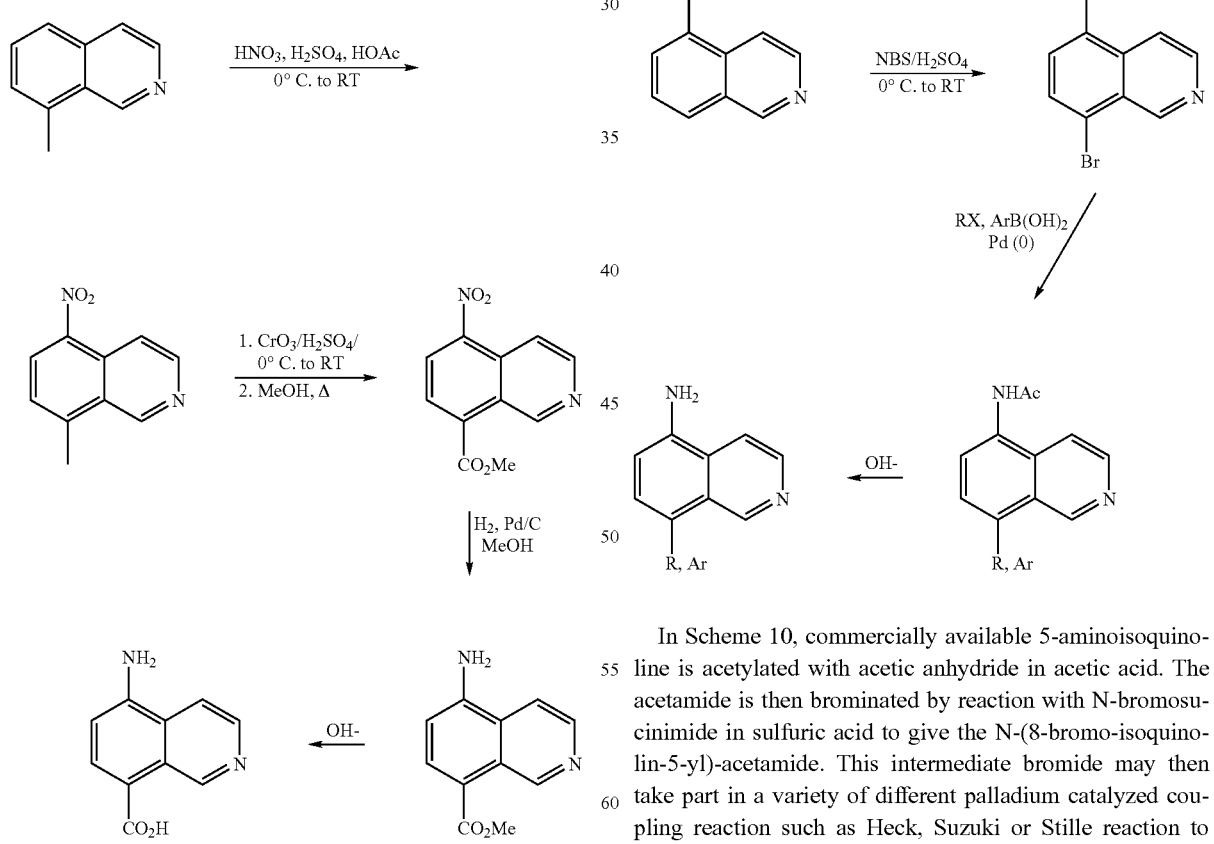

In Scheme 9, 8-methylisoquinoline is prepared by modification of the method of Yoshida et al., *Bioorg. Med. Chem.* 1999, 7, 2647. Nitration is achieved by reaction of the 8-methylisoquinoline with a nitrating agent such as potas- In Scheme 10, commercially available 5-aminoisoquinoline is acetylated with acetic anhydride in acetic acid. The acetamide is then brominated by reaction with N-bromosuccinimide in sulfuric acid to give the N-(8-bromo-isoquinolin-5-yl)-acetamide. This intermediate bromide may then take part in a variety of different palladium catalyzed coupling reaction such as Heck, Suzuki or Stille reaction to yield 8-aryl, heteroaryl, ally, vinyl etc. isoquinoline acetamides. The acetamide may be hydrolyzed to give the 5-amino-8-substituted compounds that may be further reacted as described in Schemes 5 and 6 to give the target ureas.

SCHEME 11

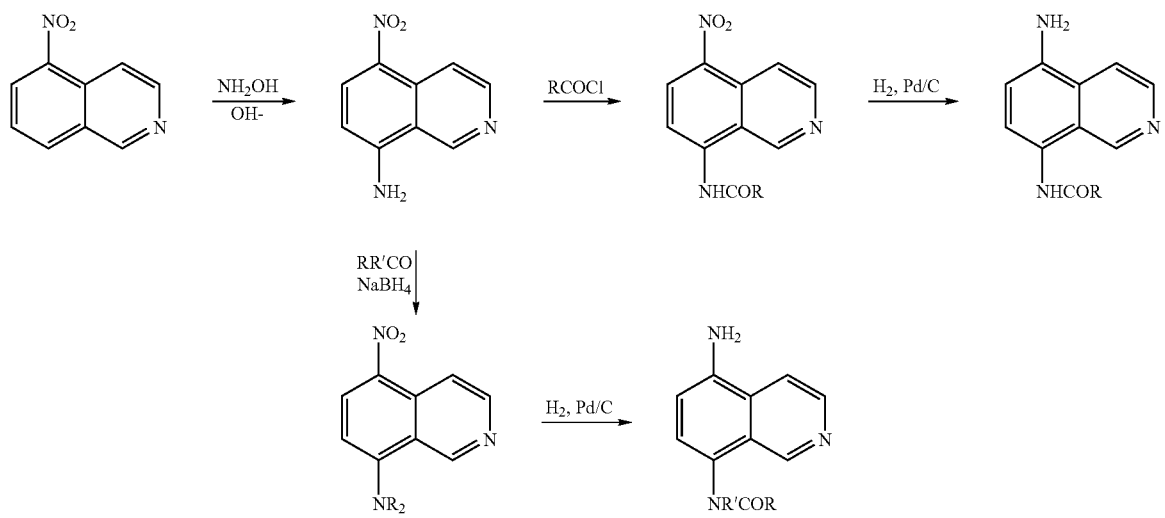

In Scheme XI, commercially available 5-nitroisoquinoline is aminated with hydroxylamine hydrochloride and sodium hydroxide in ethanol at 50° C. to yield the 5-nitro-isoquinolin-8-ylamine which may be acylated with a suitable acylating agent and then reduced by hydrogenation with a suitable catalyst or another suitable reducing agent such as tin(II) chloride to give the amino isoquinolineamide which may be further elaborated by the chemistry illustrated in Schemes 5 and 6 to the target ureas. Alternatively, the 5-nitro-isoquinolin-8-ylamine may be subjected to reductive alkylation by reaction with a suitable carbonyl compound in the presence of a suitable reducing agent such as sodium borohydride. This nitro aminoisoquinoline may be reduced by hydrogenation with a suitable catalyst or another suitable reducing agent such as tin(II) chloride and then further elaborated by the chemistry illustrated in Schemes 5 and 6 to the target ureas.

SCHEME 12

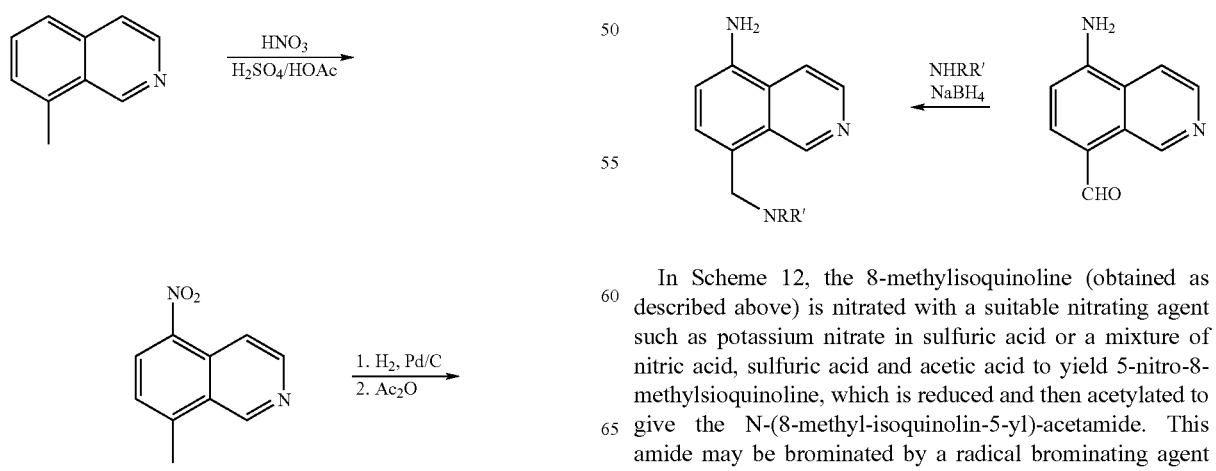

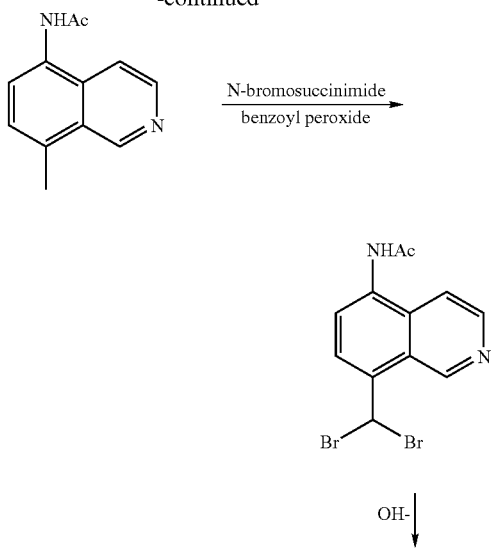

In Scheme 12, the 8-methylisoquinoline (obtained as described above) is nitrated with a suitable nitrating agent such as potassium nitrate in sulfuric acid or a mixture of nitric acid, sulfuric acid and acetic acid to yield 5-nitro-8-methylsioquinoline, which is reduced and then acetylated to give the N-(8-methyl-isoquinolin-5-yl)-acetamide. This amide may be brominated by a radical brominating agent such as N-bromosuccinimide/benzoyl peroxide to give the dibromo isoquinoline acetamide. The dibromo intermediate may then be hydrolyzed in the presence of base to yield the deprotected aldehyde aminoisoquinoline, which may be further elaborated by the chemistry illustrated in Schemes 5 and 6 to the target ureas.

Protecting group manipulations may be needed at various stages of the syntheses depending upon substituents and functional groups that are present on the reactants.

It is generally preferred that the respective product of each process step be separated from other components of the

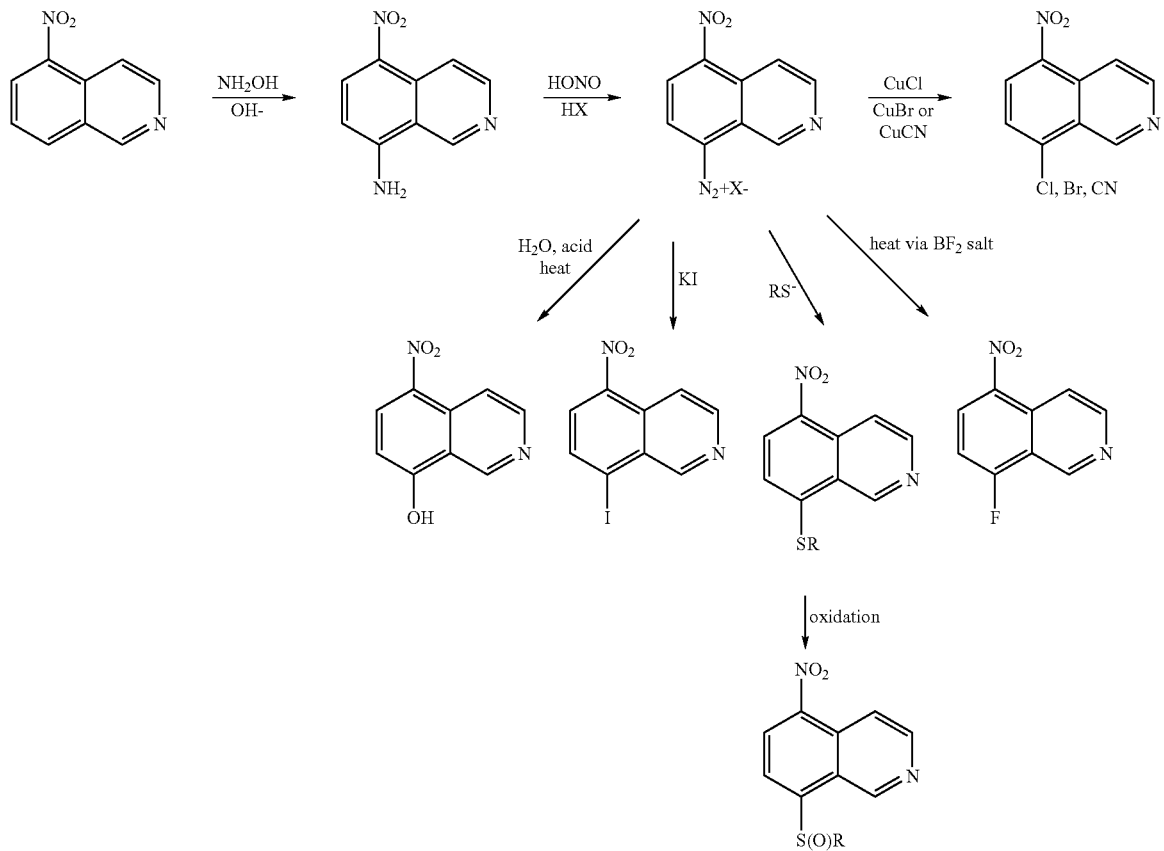

SCHEME 13

In Scheme 13, commercially available 5-nitroisoquinoline is aminated with hydroxylamine hydrochloride and sodium hydroxide in ethanol at 50° C. to yield the 5-nitroisoquinolin-8-ylamine, which may be diazotized with a mixture of sodium nitrite in a strong acid such as hydrochloric, sulfuric or hydrofluoroboric acid. The diazonium salt may be heated with an appropriate copper salt such a copper chloride, copper bromide or copper cyanide to yield the 8-Cl, 8-Br or 8-CN nitro isoquinolines respectively. The diazonium salt may also be heated in with potassium iodide to yield the 8-iodo intermediate or heated in the presence of an aqueous acid such as sulfuric acid to yield the 8-OH nitroisoquinoline. The tetrafluoroborate diazonium salt may be heated to yield the 8-F nitroisoquinoline. In addition, the diazonium salt may be reacted with a sulfur nucleophile to yield the 8-thioalkyl nitroisoquinoline which may be further oxidized to the 8-sulfoxide or 8-sulfone. Any of the nitroisoquinolines described above may then be reduced by hydrogenation with a suitable catalyst or another suitable reducing agent such as tin(II) chloride and then further elaborated by the chemistry illustrated in Schemes 5 and 6 to the target ureas.

reaction mixture and subjected to purification before its use as a starting material in a subsequent step. Separation techniques typically include evaporation, extraction, precipitation and filtration. Purification techniques typically include column chromatography (Still, W. C. et. al., *J. Org. Chem.* 1978, 43, 2921), thin-layer chromatography, crystallization and distillation. The structures of the final products, intermediates and starting materials are confirmed by spectroscopic, spectrometric and analytical methods including nuclear magnetic resonance (NMR), mass spectrometry (MS) and liquid chromatography (HPLC). In the descriptions for the preparation of compounds of this invention, ethyl ether, tetrahydrofuran and dioxane are common examples of an ethereal solvent; benzene, toluene, hexanes and cyclohexane are typical hydrocarbon solvents and dichloromethane and dichloroethane are representative halogenhydrocarbon solvents. In those cases wherein the product is isolated as the acid addition salt the free base may be obtained by techniques known to those skilled in the art. In those cases in which the product is isolated as an acid addition salt, the salt may contain one or more equivalents of the acid.

Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

EXAMPLE 1

Compound 65

Potassium phthalamide (4.104 g, 22.16 mmol) was suspended in 50 mL DMF. To the suspension was added 4-nitrobenzylbromide (4.355 g, 20.16 mmol). The reaction was stirred under nitrogen for 18 hours at which time it was poured into 400 mL water. The precipitate was collected via filtration and crystallized once from 25 mL hot acetic acid, filtered and dried to yield the product (4.833 g, 17.12 mmol) as light yellow crystalline platelets. NMR ($_{d6}$-DMSO): 8.20 (d, 2H), 7.92 (m, 4H), 7.62 (d, 2H), 4.94 (s, 2H).

To the nitro product from the previous reaction (4.63 g, 16.4 mmol) was added ethanol and 5% palladium on carbon (0.467 g). The mixture was hydrogenated at about 50 psi for 2.5 hours at which time additional catalyst (0.100 g) was added and the hydrogenation was continued for and additional 3 hours. The reaction was then filtered over a pad of celite and the filter cake rinsed with methanol and aqueous HCl until the product is dissolved away. The combined filtrates were then evaporated in vacuo to remove the methanol and ethanol present. The aqueous solution was basified with 3N NaOH and the precipitated crude product was collected by filtration. The material was titurated with 50 mL hot ethanol and filtered and dried to give the product (1.157 g, 4.59 mmol) as a tan powder. MH+=253.4; NMR ($_{d6}$-DMSO): 7.88 (m, 4H), 6.99 (d, 2H), 6.50 (d, 2H), 5.07 (br s, 2H), 4.57 (s, 2H).

The aniline from the previous reaction (1.147 g, 4.55 mmol) was suspended in 25 mL DCE. To this was added cyclohexanecarboxaldehyde (0.55 mL, 4.5 mmol) and tetramethylammonium triacetoxyborohydride (1.84 g, 6.99 mmol). The mixture was allowed to stir for 18 hours then paraformaldehyde (0.688 g, 22.9 mmol) and additional tetramethylammonium triacetoxyborohydride (1.28 g, 4.87 mmol) was added. This mixture was refluxed under a nitrogen atmosphere for 3 hours. After cooling, the reaction mixture was diluted with 25 mL DCM and washed twice with 25 mL water once with 25 mL saturated sodium bicarbonate and finally once with 25 mL brine. The organics were dried with $Na_2SO_4$, filtered and evaporated to yield the crude product that solidified upon standing. This solid was titurated with a little hexanes, filtered and dried to give the product (1.114 g, 3.07 mmol) as a yellow powder. MH+=363.6; NMR ($CDCl_3$): 7.82 (m, 2H), 7.68 (m, 2H), 7.33 (d, 2H), 6.58 (d, 2H), 4.72 (s, 2H), 3.09 (d, 2H), 2.92 (s, 3H), 1.78–1.57 (m, 6H), 1.30–1.05 (m, 3H), 1.01–0.81 (m, 2H).

To the substituted aniline from the previous reaction (1.100 g, 3.03 mmol) suspended in 20 mL ethanol was added hydrazine hydrate (0.30 mL, 6.2 mmol). The mixture was kept under a nitrogen atmosphere and refluxed for 4 hours. When cooled 50 mL ethyl acetate was added to the reaction and the solid that formed was filtered off. The filtrate was evaporated in vacuo and a little fresh ethyl acetate was added to precipitate a little more solid that was filtered off as before. The filtrate was evaporated, dissolved in hexanes and filtered one final time. Evaporation of the filtrate gave the product benzylamine (0.352 g, 1.51 mmol) as a yellow oil. MH+=233.5; NMR ($CDCl_3$): 7.16 (d, 2H), 6.63 (d, 2H), 3.77 (s, 2H), 3.12 (d, 2H), 2.96 (s, 3H), 1.81–1.61 (m, 6H), 1.40 (br s, 2H), 1.31–1.08 (m, 3H), 1.02–0.85 (m, 2H).

To quinoline-3-carboxylic acid (2.600 g, 15.01 mmol) suspended in 25 mL benzene was added triethylamine (2.3 mL, 16.5 mmol). The solution was cooled on an ice bath and to it was added DPPA (3.3 mL, 15.3 mmol). The ice bath was allowed to melt and the reaction was stirred under nitrogen for 16 hours. The reaction was then poured into 100 mL ice water and extracted three times with 50 mL diethyl ether. The combined organics were washed once with 50 mL brine, dried with $Na_2SO_4$, filtered and evaporated in vacuo to yield the product acylazide (2.842 g, 14.3 mmol) as a yellow solid. MH+=199.3; NMR ($CDCl_3$): 9.42 (s, 1H), 8.88 (s, 1H), 8.20 (d, 1H), 7.97 (d, 1H), 7.88 (t, 1H), 7.67 (t, 1H).

The acylazide from the previous reaction (2.82 g, 14.2 mmol) was suspended in 75 mL benzene. The reaction was refluxed under a nitrogen atmosphere for 3.5 hours. The reaction was concentrated in vacuo to yield the crude quinoline-3-isocyanate as a yellow powder (2.353 g, 13.8 mmol) that was carried on without further purification.

To the substituted 4-aminobenzylamine (0.172 g, 0.74 mmol) in 5 mL acetonitrile was added the quinoline-3-isocyanate. The reaction was allowed to stir for 19 hours at which time the precipitate that formed was filtered off and washed with a small amount of acetonitrile and then ethanol and dried to give the final product urea (0.077 g, 0.19 mmol) as a yellow-tan powder. MH+=403.5; NMR ($CDCl_3$): 8.57 (d, 1H), 8.48 (d, 1H), 8.00 (d, 1H), 7.74 (d, 1H), 7.58 (t, 1H), 7.50 (t, 1H), 7.21 (d, 2H), 6.64 (m, 3H), 5.06 (br t, 1H), 4.38 (d, 2H), 3.10 (d, 2H), 2.92 (s, 3H), 1.79–1.54 (m, 6H), 1.30–1.07 (m, 3H), 1.02–0.83 (m, 2H).

EXAMPLE 2

1-(1-Chloro-isoquinolin-5-yl)-3-(4-trifluoromethyl-benzyl)-urea (1-Chloro-isoquinolin-5-yl)-carbamic acid phenyl ester (150 mgs, 0.5 mmol), and 4-trifluoromethyl-benzylamine (88 mgs, 0.5 mmol) were combined and stirred overnight in DMSO (4 mL) at ambient temperature. The product was purified by directly injecting the crude reaction onto a reverse phase prep-HPLC (90–10% water:acetonitrile gradient). The appropriate fractions were lyophilized to yield 1-(1-Chloro-isoquinolin-5-yl)-3-(4-trifluoromethyl-benzyl)-urea (118 mgs, 61%) MS (MH+) 379.9; $^1$H NMR (DMSO-$_{d6}$) δ 4.47 (d, 2H, J=5.8 Hz), 7.21 (m, 1H), 7.56 (d, 2H, J=8.1 Hz), 7.71–7.76 (m, 3H), 7.93 (d, 1H, J=8.5), 8.01 (d, 1H, J=6.0 Hz), 8.34–8.36 (m, 2H), 8.95 (s, 1H). HPLC $R_t$=4.57 min (90–10% water:acetonitrile gradient, 100% pure).

EXAMPLE 3

1-(4-Chloro-3-trifluoromethyl-benzyl)-3-(7-hydroxy-naphthalen-1-yl)-urea

4-Chloro-3-trifluoromethyl-benzylamine (150 mg, 0.71 mmol) and (7-hydroxy-naphthalen-1-yl)-carbamic acid phenyl ester (200 mg, 0.7 mmol) were combined and stirred at ambient temperature in DMSO (3 mL) overnight. The product was purified by directly injecting the crude reaction onto a reverse phase prep-HPLC (90–10% water:acetonitrile gradient). The appropriate fractions were lyophilized to yield 1-(4-Chloro-3-trifluoromethyl-benzyl)-3-(7-hydroxy-naphthalen-1-yl)-urea (212.7 mg, 0.54 mmol). MS (MH$^+$) 394.9; $^1$H NMR (CD$_3$OD) δ 4.41 (s, 2H), 7.09 (dd, 1H, J=2.4 Hz), 7.21–7.26 (m, 2H), 7.46 (d, 1H, J=7.3 Hz), 7.54 (d, 2H, J=1.0 Hz), 7.62 (d, 1H, J=8.2 Hz), 7.71–7.75 (m, 2H). HPLC R$_t$=4.4 min (90–10% water:acetonitrile gradient, 100% pure).

EXAMPLE 4

1-(4-tert-Butyl-cyclohexyl)-3-(7-hydroxy-naphthalen-1-yl)-urea 4-tert-Butyl-cyclohexylamine (69 mg, 0.44 mmol) and (7-hydroxy-naphthalen-1-yl)-carbamic acid phenyl ester (125 mg, 0.44 mmol) were combined and stirred at ambient temperature in DMSO (3 mL) overnight. The product was purified by directly injecting the crude reaction onto a reverse phase prep-HPLC (90–10% water:acetonitrile gradient). The appropriate fractions were lyophilized to yield 1-(4-tert-Butyl-cyclohexyl)-3-(7-hydroxy-naphthalen-1-yl)-urea
(99 mg, 0.3 mmol). MS (MH$^+$) 341.0; $^1$H NMR (CD$_3$OD) δ 0.87 (m, 9H), 1.07–1.15 (m, 5H), 1.61 (m, 1H), 1.85 (m, 1H), 2.05 (m, 1H), 3.48 (m, 1H), 7.05–7.19 (m, 1H), 7.2–7.26 (m, 2H), 7.48–7.58 (m, 2H), 7.70–7.73 (m, 1H), HPLC R$_t$=4.8 min (90–10% water:acetonitrile gradient, 100% pure).

EXAMPLE 5

1-(7-Hydroxy-naphthalen-1-yl)-3-(5-methyl-2-trifluoromethyl-furan-3-ylmethyl)-urea (5-Methyl-2-trifluoromethyl-furan-3-yl)-methylamine (80 mg, 0.44 mmol) and (7-hydroxy-naphthalen-1-yl)-carbamic acid phenyl ester (125 mg, 0.44 mmol) were combined and stirred at ambient temperature in DMSO (3 mL) overnight. The product was purified by directly injecting the crude reaction onto a reverse phase prep-HPLC (90–10% water:acetonitrile gradient). The appropriate fractions were lyophilized to yield 1-(7-Hydroxy-naphthalen-1-yl)-3-(5-methyl-2-trifluoromethyl-furan-3-ylmethyl)-urea (130 mg, 0.35 mmol). MS (MH$^+$) 365.0; $^1$H NMR (CD$_3$OD) δ 2.3 (s, 3H), 4.32 (s, 2H), 6.21 (s, 1H), 7.08 (dd, 1H, J=2.3), 7.21–7.26 (m, 2H), 7.48 (d, 1H, J=6.4), 7.61 (d, 1H, J=8.1 Hz), 7.73 (d, 1H, J=8.8 Hz). HPLC R$_t$=4.23 min (90–10% water:acetonitrile gradient, 98% pure).

EXAMPLE 6

Compound 1

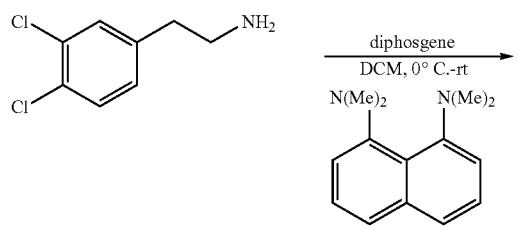

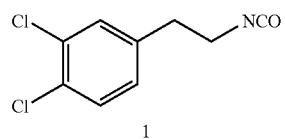

A. A solution of diphosgene (ClCO$_2$CCl$_3$) (0.01 mol, 1.97 g) in 30 mL of methylene chloride was cooled to 0° C. in an ice bath. A solution of the 3,4 dichlorophenethylamine (0.017 mol, 3.23 g) and the proton sponge (1,8-bis(dimethylamino)-naphthalene) (0.033 mol, 7.07 g) in 30 mL of DCM was added slowly to the cooled solution. The reaction mixture was stirred at 0° C. for 30 minutes, then allowed to warm to room temperature and stirred at room temperature for an additional 30 minutes. The reaction mixture was then evaporated in vacuo. The residue was taken up in 40 mL of DCM and washed sequentially with 40 mL 1N HCl, 40 mL NaOH, and 40 mL brine. The organic phase was dried over Na$_2$SO$_4$ and evaporated in vacuo to a thick bright yellow oil (0.009 mol, 1.9 g). This oil was used without further purification in the next reaction. MS (MH+): 215; $^1$H NMR (CDCl$_3$): δ 2.8–2.9 (t, 2H), 3.5–3.6 (t, 2H), 7.0 (m, 1H), 7.4–7.6 (m, 2H).

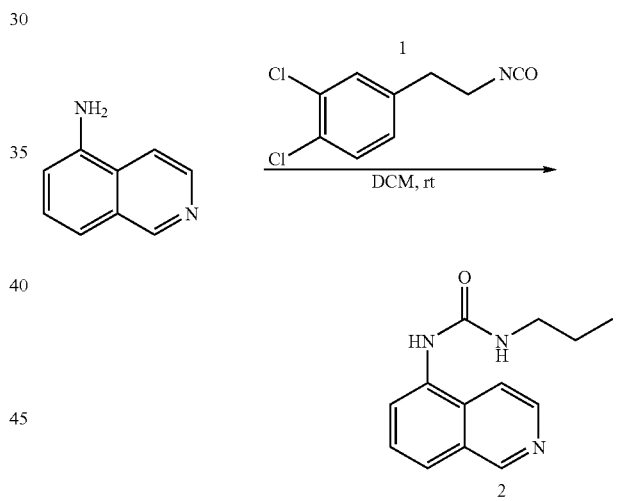

B. 5-Aminoisoquinoline (0.005 mol, 0.72 g) was dissolved in 40 mL of methylene chloride. The isocyanate 1 (0.0055 mol, 1.19 g) obtained in step A was slowly added via syringe to the stirred solution. The reaction mixture was stirred at room temperature for 16 hours. The reaction mixture was evaporated in vacuo. The residue was taken up in 40 mL of DCM and washed with 40 mL saturated sodium bicarbonate and then 40 mL water. The organic phase was dried over Na$_2$SO$_4$ and evaporated in vacuo. The solid obtained was triturated 3 times with 20 mL hexane each time. The product was then recrystallized from acetone to yield the title compound 2 as a chalky white powder, (0.0036 mol, 1.3 g). MS (MH+): 360.2; $^1$H NMR (DMSO-$d_6$): δ 2.8 (t, 2H), 3.4 (t, 2H), 6.6 (t, 1H), 7.2 (d, 1H), 7.5–7.6 (m, 3H), 7.7 (d, 1H), 7.8 (d, 1H), 8.2 (d, 1H), 8.5 (d, 1H), 8.6 (s, 1H), 9.1 (s, 1H); C$_{18}$H$_{15}$Cl$_2$N$_3$O

|   | Calc | Found |
|---|------|-------|
| C | 60.01 | 59.97 |
| H | 4.20 | 4.18 |
| N | 11.66 | 11.65 |

EXAMPLE 7

Compound 4

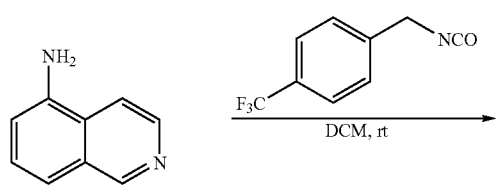

A. 5-Aminoisoquinoline (0.01 mol, 1.44 g) was dissolved in 65 mL of methylene chloride. 4-Trifluoromethyl benzylisocyanate (prepared as described above using 4-trifluoromethyl benzylamine), (0.011 mol, 2.21 g) was slowly added via syringe to the stirred solution. The reaction mixture was stirred at room temperature for 16 hours. A precipitate was evident which was collected by vacuum filtration. The collected solid was triturated with hexane (2×20 mL). The product was recrystallized from ethyl acetate to yield the title compound 1 as a pale yellow powdery solid (0.006 mol, 2.1 g). MS (MH+): 346.1; $^1$H NMR (MeOH-d$_4$): δ 4.4 (s, 2H), 7.4–7.6 (m, 5H), 7.7 (d, 1H), 7.8 (d, 1H), 8.1 (d, 1H), 8.3 (d, 1H), 9.1 (s, 1H).

EXAMPLE 8

1-(8-Hydroxy-isoquinolin-5-yl)-3-(4-methyl-3-trifluoromethyl-benzyl)-urea hydrochloride Compound 69

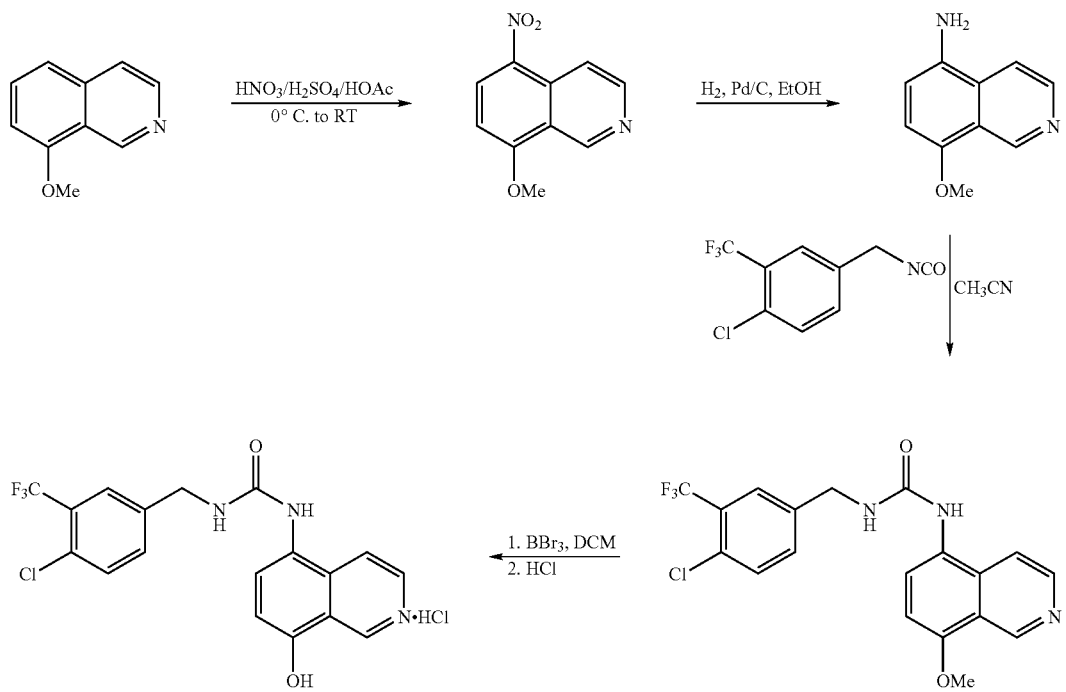

A. 8-Methoxyisoquinoline, obtained as described by Yoshida et al., *Bioorg. Med. Chem*. 1999, 7, 2647, (3.197 g, 20.0 mmol) was dissolved in 20 mL glacial acetic acid with stirring. The solution was cooled on an ice bath to 0° C. and 20 mL concentrated sulfuric acid was added. This addition caused the temperature to rise to 40–45° C. When the temperature had cooled back down to 0° C., concentrated nitric acid (1.9 mL, 30 mmol) was added dropwise which caused the temperature of the reaction mixture to rise to 12–13° C. When the temperature cooled back down the ice bath was removed and the reaction was stirred at room temperature for 2 hours. The reaction mixture was then poured onto ice and the resulting mixture basified with 100 mL concentrated ammonium hydroxide. The precipitate that formed was collected by filtration, rinsed with water and dried under vacuum to yield the yellow product as a 2:1 mixture of 8-methoxy-5-nitro-isoquinoline and 8-methoxy-7-nitro-isoquinoline, respectively (3.776 g, 18.5 mmol); MS: M+H$^+$=205.1.

B. The isomerically mixed nitro methoxy isoquinoline from step A (2.71 g, 13.3 mmol) was suspended in 150 mL ethanol containing 0.271 g 5% Pd/C. The mixture was hydrogenated at ~50 psi for 3 hours then quickly filtered over a pad of celite and evaporated under vacuum to yield a mixture of 8-methoxy-isoquin-5-ylamine and 8-methoxy-isoquin-7-ylamine as an orange solid (2.30 g, 13.2 mmol); MS: M+H$^+$=175.2.

C. The isomerically mixed amino methoxy isoquinoline from step B (13.2 mmol) was suspended in 50 mL acetonitrile. A solution of 4-Cl-3-CF$_3$-benzylisocyanate (3.46 g, 14.7 mmol) in 50 mL acetonitrile was added to the isoquinoline suspension in one portion. The reaction immediately became a homogeneous solution then after stirring for 5 minutes a precipitate began to form. The reaction was stirred at room temperature overnight, the precipitate was isolated by filtration, rinsed with acetonitrile and air-dried. The desired product, 1-(4-chloro-3-trifluoromethyl-benzyl)-3-(8-methoxy-isoquinolin-5-yl)-urea5-urea isomer was isolated as a lite tan solid (3.514 g, 8.6 mmol). Note: the desired product precipitated out of the reaction mixture whereas the undesired isomeric product remained in the filtrate. $^1$H NMR (d6-DMSO): δ 9.48 (s, 1H), 8.57 (d, 1H), 8.52 (s, 1H), 7.88 (d, 1H), 7.82 (m, 2H), 7.73 (d, 1H), 7.64 (d, 1H), 7.09 (d, 1H), 7.00 (t, 1H), 4.40 (d, 2H), 4.01 (s, 3H); MS: M+H$^+$=410.1.

D. The 1-(4-chloro-3-trifluoromethyl-benzyl)-3-(8-methoxy-isoquinolin-5-yl)-urea from step C (2.048 g, 5.00 mmol) was suspended in 50 mL methylene chloride with stirring. The suspension was cooled on an ice bath and BBr$_3$ solution (1M in DCM, 25 mL, 25 mmol) was added dropwise over 9 minutes. The reaction mixture immediatelt formed a gooey solid. The ice bath was removed, the reaction was stirred overnight at room temperature then heated at reflux for 1.5 hours. The reaction mixture was quenched with an excess of MeOH and evaporated in vacuo. Methanol was added to the residue and it was again evaporated in vacuo. This procedure was repeated, the residue was suspended in 50 mL 2N HCl and heated to reflux for several minutes. After cooling, the solid that formed was collected by filtration, air-dried, dissolved in MeOH, evaporated in vacuo to a residue, triturated with 50 mL acetonitrile and finally isolated by filtration. This material was purified by reversed-phase chromatography (25–60% acetonitrile in water+0.1% TFA). The proper fractions were pooled and lyophilized to give the product trifluoroacetate salt as a fluffy yellow solid (0.57 g). The TFA salt was dissolved in MeOH/DCM, treated with excess ethereal HCl and evaporated in vacuo. This treatment was repeated two times. The resulting solid was triturated with hexanes, filtered and dried under a stream of nitrogen. The resulting hydrochloride salt of the title compound, 1-(8-hydroxy-isoquinolin-5-yl)-3-(4-methyl-3-trifluoromethyl-benzyl)-urea, was obtained as a yellow powder (0.443 g, 1.00 mmol); $^1$H NMR (d6-DMSO): δ 11.62 (s, 1H), 9.70 (s, 1H), 9.02 (s, 1H), 8.58 (d, 1H), 8.32 (d, 1H), 8.13 (d, 1H), 7.81 (s, 1H), 7.73 (d, 1H), 7.67 (d, 1H), 7.34 (t, 1H), 7.26 (d, 1H), 4.41 (d, 2H); MS: M+H$^+$=396.0.

Elemental Analysis Calculated for .HCl.½H$_2$O: C=49.00; H=3.43; N=9.53; Cl=16.07; F=12.92; KF=2.05.

Elemental Analysis Found: C=48.63; H=3.20; N=9.29; Cl=16.25; F=12.84; KF=2.16.

Using the procedures of the Examples above and the appropriate reagents, starting materials and purification methods known to those skilled in the art, other compounds of the present invention may be prepared including, but not limited to:

TABLE 1

Mass Spectral Data for Selected Compounds

| Cmpd No. | Substituents on Formula (Ia) | Mass Calc | Parent Ion |
|---|---|---|---|
| 1 | $R_1$ is H, $R_2$ is H, $R_3$ is H, $R_4$ is H, $R_5$ is H, L is —CH$_2$CH$_2$—, $R_6$ is (3,4-diCl)Ph, X is N, and Y is C; | 360.2 | 360.2 |
| 2 | $R_1$ is H, $R_2$ is H, $R_3$ is H, $R_4$ is H, $R_5$ is H, L is —CH$_2$CH$_2$—, $R_6$ is (3-CF$_3$)Ph, X is N, and Y is C; | 359.3 | 360.5 |
| 3 | $R_1$ is H, $R_2$ is H, $R_3$ is H, $R_4$ is H, $R_5$ is H, L is —CH$_2$CH$_2$—, $R_6$ is (4-Cl)Ph, X is N, and Y is C; | 325.8 | 326.0 |
| 4 | $R_1$ is H, $R_2$ is H, $R_3$ is H, $R_4$ is H, $R_5$ is H, L is —CH$_2$—, $R_6$ is (4-CF$_3$)Ph, X is N, and Y is C; | 345.3 | 346.4 |
| 5 | $R_1$ is H, $R_2$ is H, $R_3$ is H, $R_4$ is H, $R_5$ is H, L is —CH$_2$—, $R_6$ is (3,4-diCl)Ph, X is N, and Y is C; | 346.2 | 346.2 |
| 6 | $R_1$ is H, $R_2$ is H, $R_3$ is H, $R_4$ is H, $R_5$ is H, L is —CH$_2$—, $R_6$ is (4-Cl)Ph, X is N, and Y is C; | 311.8 | 312.2 |
| 7 | $R_1$ is H, $R_2$ is H, $R_3$ is H, $R_4$ is H, $R_5$ is H, L is —CH$_2$—, $R_6$ is (3-CF$_3$)Ph, X is N, and Y is C; | 345.4 | 346.5 |
| 8 | $R_1$ is Me, $R_2$ is H, $R_3$ is H, $R_4$ is H, $R_5$ is H, L is —CH$_2$—, $R_6$ is (3,4-diCl)Ph, X is N, and Y is C; | 360.3 | 360.2 |

TABLE 1-continued

Mass Spectral Data for Selected Compounds

| Cmpd No. | Substituents on Formula (Ia) | Mass Calc | Parent Ion |
|---|---|---|---|
| 9 | $R_1$ is Me, $R_2$ is H, $R_3$ is H, $R_4$ is H, $R_5$ is H, L is —$CH_2$—, $R_6$ is (3-$CF_3$)Ph, X is N, and Y is C; | 359.4 | 360.5 |
| 10 | $R_1$ is H, $R_2$ is H, $R_3$ is H, $R_4$ is H, $R_5$ is H, L is —$CH_2$CH((4-OMe)Ph)—, $R_6$ is Pyridin-3-yl, X is N, and Y is C; | 412.5 | 412.9 |
| 11 | $R_1$ is H, $R_2$ is H, $R_3$ is H, $R_4$ is H, $R_5$ is H, L is —$CH_2$CH(—$CH_2$Ph)—, $R_6$ is (4-OMe)Ph, X is N, and Y is C; | 411.5 | 412.5 |
| 12 | $R_1$ is H, $R_2$ is H, $R_3$ is H, $R_4$ is H, $R_5$ is H, L is —$CH_2$CH(—$CH_2$cyclohexyl)—, $R_6$ is (4-OMe)Ph, X is N, and Y is C; | 417.6 | 418.5 |
| 13 | $R_1$ is OH, $R_2$ is H, $R_3$ is H, $R_4$ is H, $R_5$ is H, L is —$CH_2$—, $R_6$ is (4-t-Bu)Ph, X is C and Y is C; | 348.4 | 349.1 |
| 14 | $R_1$ is OH, $R_2$ is H, $R_3$ is H, $R_4$ is H, $R_5$ is H, L is —$CH_2$—, $R_6$ is (4-Cl)Ph, X is C and Y is C; | 326.8 | 326.9 |
| 15 | $R_1$ is OH, $R_2$ is H, $R_3$ is H, $R_4$ is H, $R_5$ is H, L is —$CH_2$—, $R_6$ is Pyridin-3-yl, X is C and Y is C; | 293.3 | 294.2 |
| 16 | $R_1$ is OH, $R_2$ is H, $R_3$ is H, $R_4$ is H, $R_5$ is H, L is —$CH_2$—, $R_6$ is (4-$OCF_3$)Ph, X is C and Y is C; | 376.3 | 377.0 |
| 17 | $R_1$ is OH, $R_2$ is H, $R_3$ is H, $R_4$ is H, $R_5$ is H, L is —$CH_2$—, $R_6$ is (4-$CF_3$)Ph, X is C and Y is C; | 360.3 | 361.0 |
| 18 | $R_1$ is OH, $R_2$ is H, $R_3$ is H, $R_4$ is H, $R_5$ is H, L is —$CH_2$—, $R_6$ is Ph, X is C and Y is C; | 292.3 | 293.0 |
| 19 | $R_1$ is OH, $R_2$ is H, $R_3$ is H, $R_4$ is H, $R_5$ is H, L is —$CH_2$—, $R_6$ is (3-$CF_3$)Ph, X is C and Y is C; | 360.3 | 361.0 |
| 20 | $R_1$ is H, $R_2$ is H, $R_3$ is H, $R_4$ is H, $R_5$ is H, L is —$CH_2$—, $R_6$ is (3-$CF_3$-4-Cl)Ph, X is N, and Y is C; | 379.1 | 379.7 |
| 21 | $R_1$ is H, $R_2$ is H, $R_3$ is H, $R_4$ is H, $R_5$ is H, L is —$CH_2CH_2$—, $R_6$ is (4-OMe)Ph, X is N, and Y is C; | | |
| 22 | $R_1$ is H, $R_2$ is H, $R_3$ is H, $R_4$ is H, $R_5$ is H, L is —$CH_2$—, $R_6$ is (4-$OCF_3$)Ph, X is N, and Y is C; | 361.6 | 362.1 |
| 23 | $R_1$ is OH, $R_2$ is H, $R_3$ is H, $R_4$ is H, $R_5$ is H, L is —$CH_2CH_2$—, $R_6$ is Ph, X is C and Y is C; | 306.4 | 307.0 |
| 24 | $R_1$ is OH, $R_2$ is H, $R_3$ is H, $R_4$ is H, $R_5$ is Et, L is —$CH_2$—, $R_6$ is Ph, X is C and Y is C; | 320.4 | 321.0 |
| 25 | $R_1$ is OH, $R_2$ is H, $R_3$ is H, $R_4$ is H, $R_5$ is Benzyl, L is —$CH_2$—, $R_6$ is Ph, X is C and Y is C; | 382.5 | 383.0 |
| 26 | $R_1$ is OH, $R_2$ is H, $R_3$ is H, $R_4$ is H, $R_5$ is Me, L is —$CH_2$—, $R_6$ is Ph, X is C and Y is C; | 306.4 | 307.0 |
| 27 | $R_1$ is OH, $R_2$ is H, $R_3$ is H, $R_4$ is H, $R_5$ is H, L is —$CH_2CH_2$—, $R_6$ is (3,4-diCl)Ph, X is C and Y is C; | 375.2 | 376.8 |
| 28 | $R_1$ is OH, $R_2$ is H, $R_3$ is H, $R_4$ is H, $R_5$ is —$CH_2CH_2$PH, L is —$CH_2$—, $R_6$ is Ph, X is C and Y is C; | 396.5 | 397.6 |
| 29 | $R_1$ is OH, $R_2$ is H, $R_3$ is H, $R_4$ is H, $R_5$ is H, L is —$CH_2$—, $R_6$ is (6-$CF_3$)Pyridin-3-yl, X is C and Y is C; | 361.3 | 361.9 |
| 30 | $R_1$ is OH, $R_2$ is H, $R_3$ is H, $R_4$ is H, $R_5$ is Me, L is —$CH_2$—, $R_6$ is (3,4-diCl)Ph, X is C and Y is C; | 375.2 | 377.1 |
| 31 | $R_1$ is OH, $R_2$ is H, $R_3$ is H, $R_4$ is H, $R_5$ is H, L is —$CH_2$—, $R_6$ is (3,4-diCl)Ph, X is C and Y is C; | 361.2 | 362.4 |
| 32 | $R_1$ is OH, $R_2$ is H, $R_3$ is H, $R_4$ is H, $R_5$ is H, L is —$CH_2$—, $R_6$ is Benzimidazol-2-yl, X is C and Y is C; | 332.4 | 333.3 |
| 33 | $R_1$ is H, $R_2$ is H, $R_3$ is H, $R_4$ is H, $R_5$ is H, L is —$CH_2$—, $R_6$ is (4-t-Bu)Ph, X is N, and Y is C; | 333.4 | 334.2 |
| 34 | $R_1$ is H, $R_2$ is H, $R_3$ is H, $R_4$ is H, $R_5$ is H, L is —$CH_2CH_2$—, $R_6$ is Ph, X is N, and Y is C; | 291.4 | 292.5 |
| 35 | $R_1$ is H, $R_2$ is H, $R_3$ is H, $R_4$ is H, $R_5$ is H, L is —$CH_2CH_2$—, $R_6$ is (4-t-Bu)Ph, X is N, and Y is C; | 347.5 | 348.2 |
| 36 | $R_1$ is H, $R_2$ is H, $R_3$ is H, $R_4$ is H, $R_5$ is H, L is —$CH_2CH_2$—, $R_6$ is (4-$CF_3$)Ph, X is N, and Y is C; | 359.4 | 360.3 |
| 37 | $R_1$ is H, $R_2$ is H, $R_3$ is H, $R_4$ is H, $R_5$ is H, L is —$CH_2$—, $R_6$ is (4-OMe)Ph, X is N, and Y is C; | 307.3 | 308.1 |
| 38 | $R_1$ is H, $R_2$ is H, $R_3$ is H, $R_4$ is H, $R_5$ is H, L is —$CH_2CH_2$—, $R_6$ is (4-$OCF_3$)Ph, X is N, and Y is C; | 357.4 | 376.2 |
| 39 | $R_1$ is OH, $R_2$ is H, $R_3$ is H, $R_4$ is H, $R_5$ is H, L is —$CH_2$—, $R_6$ is (5-thiophen-2-yl)Thiophen-2-yl, X is C and Y is C; | 380.5 | 380.7 |
| 40 | $R_1$ is OH, $R_2$ is H, $R_3$ is H, $R_4$ is H, $R_5$ is H, L is —$CH_2$—, $R_6$ is Benzthiophen-2-yl, X is C and Y is C; | 348.4 | 348.8 |
| 41 | $R_1$ is OH, $R_2$ is H, $R_3$ is H, $R_4$ is H, $R_5$ is H, L is —$CH_2$—, $R_6$ is (2-Br)Ph, X is C and Y is C; | 371.2 | 372.8 |
| 42 | $R_1$ is OH, $R_2$ is H, $R_3$ is H, $R_4$ is H, $R_5$ is H, L is —$CH_2$—, $R_6$ is (3,4-diF)Ph, X is C and Y is C; | 328.3 | 329.0 |

TABLE 1-continued

Mass Spectral Data for Selected Compounds

| Cmpd No. | Substituents on Formula (Ia) | Mass Calc | Parent Ion |
|---|---|---|---|
| 43 | $R_1$ is OH, $R_2$ is H, $R_3$ is H, $R_4$ is H, $R_5$ is H, L is —$CH_2$—, $R_6$ is (5-Cl)Benzthiophen-3-yl, X is C and Y is C; | 382.8 | 382.9 |
| 44 | $R_1$ is OH, $R_2$ is H, $R_3$ is H, $R_4$ is H, $R_5$ is H, L is —$CH_2CH_2$—, $R_6$ is (2-Cl)Ph, X is C and Y is C; | 340.8 | 340.9 |
| 45 | $R_1$ is OH, $R_2$ is H, $R_3$ is H, $R_4$ is H, $R_5$ is H, L is —$CH_2$—, $R_6$ is (2,6-diCl)Ph, X is C and Y is C; | 361.2 | 362.7 |
| 46 | $R_1$ is OH, $R_2$ is H, $R_3$ is H, $R_4$ is H, $R_5$ is H, L is —$CH_2CH_2$—, $R_6$ is (4-$SO_2NH_2$)Ph, X is C and Y is C; | 385.4 | 385.7 |
| 47 | $R_1$ is OH, $R_2$ is H, $R_3$ is H, $R_4$ is H, $R_5$ is H, L is —$CH_2$—, $R_6$ is (2,4-diCl)Ph, X is C and Y is C; | 361.2 | 362.8 |
| 48 | $R_1$ is OH, $R_2$ is H, $R_3$ is H, $R_4$ is H, $R_5$ is H, L is —$CH_2$—, $R_6$ is (5-Pyridin-2-yl)Thiophene-2-yl, X is C and Y is C; | 375.5 | 376.0 |
| 49 | $R_1$ is OH, $R_2$ is H, $R_3$ is H, $R_4$ is H, $R_5$ is H, L is —$CH_2$—, $R_6$ is Pyridin-2-yl, X is C and Y is C; | 293.3 | 293.9 |
| 50 | $R_1$ is OH, $R_2$ is H, $R_3$ is H, $R_4$ is H, $R_5$ is H, L is —$CH_2CH(Ph)$—, $R_6$ is Ph, X is C and Y is C; | 382.5 | 383.6 |
| 51 | $R_1$ is OH, $R_2$ is H, $R_3$ is H, $R_4$ is H, $R_5$ is H, L is —$CH_2CH_2CH_2$—, $R_6$ is Morpholin-1-yl, X is C and Y is C; | 329.4 | 330.3 |
| 52 | $R_1$ is OH, $R_2$ is H, $R_3$ is H, $R_4$ is H, $R_5$ is H, L is —$CH_2$—, $R_6$ is 6,6-DiMe,thyl-bicyclo[3.1.1]heptan-2-yl, X is C and Y is C; | 338.4 | 339.0 |
| 53 | $R_1$ is OH, $R_2$ is H, $R_3$ is H, $R_4$ is H, $R_5$ is H, L is —$CH_2$—, $R_6$ is Cyclohexyl, X is C and Y is C; | 298.4 | 299.0 |
| 54 | $R_1$ is OH, $R_2$ is H, $R_3$ is H, $R_4$ is H, $R_5$ is H, L is —$CH_2CH_2$—, $R_6$ is Pyridin-2-yl, X is C and Y is C; | 307.3 | 308.2 |
| 55 | $R_1$ is H, $R_2$ is Cl, $R_3$ is H, $R_4$ is H, $R_5$ is H, L is —$CH_2$—, $R_6$ is (4-$CF_3$)Ph, X is N, and Y is C; | 379.8 | 379.9 |
| 56 | $R_1$ is OH, $R_2$ is H, $R_3$ is H, $R_4$ is H, $R_5$ is H, L is —$CH_2$—, $R_6$ is (3-$CF_3$-4-F)Ph, X is C and Y is C; | 378.3 | 379.1 |
| 57 | $R_1$ is OH, $R_2$ is H, $R_3$ is H, $R_4$ is H, $R_5$ is H, L is —$CH_2$—, $R_6$ is (3-$CF_3$-4-Cl)Ph, X is C and Y is C; | 394.8 | 394.9 |
| 58 | $R_1$ is OH, $R_2$ is H, $R_3$ is H, $R_4$ is H, $R_5$ is H, L is —$CH_2$—, $R_6$ is (3,5-di$CF_3$)Ph, X is C and Y is C; | 428.3 | 428.9 |
| 59 | $R_1$ is H, $R_2$ is H, $R_3$ is Cl, $R_4$ is H, $R_5$ is H, L is —$CH_2$—, $R_6$ is (4-$CF_3$)Ph, X is N, and Y is C; | 379.8 | 380.0 |
| 60 | $R_1$ is OH, $R_2$ is H, $R_3$ is H, $R_4$ is H, $R_5$ is H, L is —CH(Me)—, $R_6$ is (3-$CF_3$-4-Cl)Ph, X is C and Y is C; | 331.3 | 332.5 |
| 61 | $R_1$ is OH, $R_2$ is H, $R_3$ is H, $R_4$ is H, $R_5$ is H, L is —CH(Ph)$CH_2$—, $R_6$ is Ph, X is C and Y is C; | 345.3 | 346.1 |
| 62 | $R_1$ is OH, $R_2$ is H, $R_3$ is H, $R_4$ is H, $R_5$ is H, L is —$CH_2$—, $R_6$ is (2,4-diCl)Ph, X is C and Y is C; | 346.2 | 346.2 |
| 63 | $R_1$ is H, $R_2$ is H, $R_4$ is H, $R_5$ is H, L is $R_6$ is (3-$CF_3$)Ph, Z is O, X is C and Y is C; | 360.2 | 360.0 |
| 64 | $R_1$ is H, $R_2$ is H, $R_4$ is H, $R_5$ is H, L is —$CH_2$—, $R_6$ is (4-$CF_3$)Ph, Z is O, X is C and Y is C; | 376.5 | 377.4 |
| 65 | $R_1$ is H, $R_2$ is H, $R_4$ is H, $R_5$ is H, L is —$CH_2$—, $R_6$ is (3,4-diCl)Ph, Z is O, X is C and Y is C; | 402.5 | 403.5 |
| 66 | $R_1$ is H, $R_2$ is H, $R_4$ is H, $R_5$ is H, L is —$CH_2CH_2$—, $R_6$ is (3,4-diCl)Ph, Z is O, X is C and Y is C; | 374.3 | 345.1 |
| 67 | $R_1$ is H, $R_2$ is H, $R_4$ is H, $R_5$ is H, L is —$CH_2$—, $R_6$ is (4-N(Me,)n-pentyl)Ph, Z is O, X is C and Y is C; | 382.5 | 383.2 |
| 68 | $R_1$ is H, $R_2$ is H, $R_4$ is H, $R_5$ is H, L is —$CH_2$—, $R_6$ is (4-N(Me,)$CH_2$cyclohexyl)Ph, Z is O, X is C and Y is C; | 361.2 | 362.8 |
| 69 | $R_1$ is $OCH_3$, $R_2$ is H, $R_3$ is H, $R_4$ is H, $R_5$ is H, L is —$CH_2$—, $R_6$ is (4-Cl-3-$CF_3$) Ph, X is N | 409.8 | 410.0 |
| 70 | $R_1$ is $OCH_3$, $R_2$ is H, $R_3$ is H, $R_4$ is H, $R_5$ is H, L is —$CH_2$—, $R_6$ is (4-$CF_3$) Ph, X is N | 375.4 | 376.1 |
| 71 | $R_1$ is Cl, $R_2$ is H, $R_3$ is H, $R_4$ is H, $R_5$ is H, L is —$CH_2$—, $R_6$ is (4-$CF_3$) Ph, X is N | 379.8 | 380.0 |
| 72 | $R_1$ is Cl, $R_2$ is H, $R_3$ is H, $R_4$ is H, $R_5$ is H, L is —$CH_2$—, $R_6$ is (4-Cl-3-$CF_3$) Ph, X is N | 414.2 | 414.0 |
| 73 | $R_1$ is Cl, $R_2$ is H, $R_3$ is H, $R_4$ is H, $R_5$ is H, L is —$CH_2$—, $R_6$ is (3,4 diCl) Ph, X is N | 380.7 | 380.0 |
| 74 | $R_1$ is Cl, $R_2$ is H, $R_3$ is H, $R_4$ is H, $R_5$ is H, L is —$CH_2$—, $R_6$ is (4-t-butyl) Ph, X is N | 367.9 | 368.0 |
| 75 | $R_1$ is Cl, $R_2$ is H, $R_3$ is H, $R_4$ is H, $R_5$ is H, L is —$CH_2$—$CH_2$—, $R_6$ is (4-t-butyl) Ph, X is N | 381.9 | 382.0 |
| 76 | $R_1$ is Cl, $R_2$ is H, $R_3$ is H, $R_4$ is H, $R_5$ is H, L is —$CH_2$—$CH_2$—, $R_6$ is (3,4-diCl) Ph, X is N | 394.7 | 393.9 |

BIOLOGICAL EXAMPLES

Example 1

Human or Rat $VR_1$ Binding Assay

Compounds of the present invention were tested for their ability to inhibit the binding of [$^3$H] RTX to hVR1 receptors in a [$^3$H] RTX binding assay as previously described (Zhang, Sui-Po. Improved ligand binding assays for vanilloid receptors. PCT Int. Appl. (2002), 29 pp. CODEN: PIXXD2 WO 0233411 A1 20020425 AN 2002:315209; Grant, Elfrida R.; Dubin, Adrienne E.; Zhang, Sui-Po; Zivin, Robert A.; Zhong, Zhong Simultaneous intracellular calcium and sodium flux imaging in human vanilloid receptor 1 (VR1)-transfected human embryonic kidney cells: a method to resolve ionic dependence of VR1-mediated cell death. Journal of Pharmacology and Experimental Therapeutics (2002), 300(1), 9–17.)

HEK293 cells were transfected with human VR1 vanilloid receptors and washed with Hank's Balanced Salt Solution, dissociated with cell dissociation buffer (Sigma), and then centrifuged at 1000×g for 5 min. Cell pellets were homogenized in cold 20 mM HEPES buffer, pH 7.4, containing 5.8 mM NaCl, 320 mM sucrose, 2 mM $MgCl_2$, 0.75 $CaCl_2$ and 5 mM KCl and centrifuged at 1000×g for 15 min. The resultant supernate was then centrifuged at 40000×g for 15 min. The pelleted membranes were kept in an −80° C. freezer.

Approximately 120 μg protein/ml from membranes were incubated with indicated concentrations of [$^3$H] RTX in 0.5 ml of the HEPES buffer (pH 7.4) containing 0.25 mg/mL fatty acid-free bovine serum albumin at 37° C. for 60 min. The reaction mixture was then cooled to 4° C., 0.1 mg $\alpha_1$-acid glycoprotein added to each sample and incubated at 4° C. for 15 min. The samples were centrifuged at 18500×g for 15 min. The tip of the microcentrifuge tube containing the pellet was cut off. Bound radioactivity was quantified by scintillation counting. Non-specific binding was tested in the presence of 200 nM unlabeled RTX.

Alternatively, a binding assay using rat tissue was used. Rat spinal cord was homogenized twice with a Polytron and centrifuged at 3000 rpm for 10 min in HEPES buffer containing 20 mM HEPES, pH 7.4, NaCl 5.8 mM, sucrose 320 mM, $MgCl_2$ 2 mM, $CaCl_2$ 0.75 mM and KCl 5 mM. The supernatant was then centrifuged at 18,000 rpm for 20 min. The pellet was saved in a tube and 10 ml assay buffer was added into the tube. The pellet and buffer were mixed with a Polytron. The assay contained 120 μg/ml membrane protein and 0.3–0.6 nM [$^3$H]-RTX (NEN, Boston) in a total volume of 0.5 ml HEPES buffer. Following-incubation for 60 min at 37 C, the samples were cooled down on ice, and 100 mg of α-acid glycoprotein were added into the samples. After centrifugation at 13,000 rpm for 15 min, the supernatant was aspirated and the tips of tubes were cut off and placed into 6 ml vials. Data were calculated according to the equation: % inhibition=(total binding−binding)*100/(total binding−non specific binding). Ki value values were calculated using a Prism program.

Example 2

Human $VR_1$ Functional Assay

The functional activity of the test compounds was determined by measuring changes in intracellular calcium concentration using a $Ca^{++}$-sensitive fluorescent dye and FLIPR™ technology. Increases in $Ca^{++}$ concentration were readily detected upon challenge with capsaicin.

Example 3

Broadly Stimulated Recombinant Human VR1 and Rat VR1 Functional Assays

When nociceptors are exposed to tissue damaging stimuli, VR1 receptors are activated by a plethora of stimuli. In an effort to identify potent and efficacious antagonists at human and rat VR1 that were active under conditions simulating aspects of in vivo inflammation functional assays were developed using FLIPR to determine antagonist activity against endogenous activators and stimuli likely to be present in inflammation. Cell lines were constructed that stably expressed recombinant rat VR1 (rVR1/HEK293). Cells were exposed to various stimuli at their $EC_{80}$, with the exception of the low pH and DTT stimuli.

Low pH (pH 5.9 (rat) or pH 6.5 (human). Cells were challenged for 5 min with low pH solution which produced an increase in intracellular $Ca^{2+}$ which was subsequently reduced by exposure to antagonists. After 3 min, other stimuli (a phorbol ester to induce phosphorylation, capsaicin, anandamide, redox agents) were applied to the cells to determine the potency of antagonists to block those stimuli in an acidic environment. Cells were maintained in low pH in all steps subsequent to the calcium dye loading step.

Phoshorylation by PKC. Previous studies have suggested that phorbol esters activate VR1 via PKC phosphorylation [Premkumar, 2000 #697; Vellani, 2001 #739]. These studies were corroborated and further studies were performed to confirm that the phorbol ester effect was not due to direct effects on the channel. The role of PKC was shown pharmacologically: phorbol-12-myristate-13-acetate (PMA) and other phorbol esters active at PKC (but not the inactive 4α-phorbol) caused an increase in intracellular $Ca^{2+}$ that was mediated by VR1. The rank order potency for the panel of phorbol esters was similar to their rank order potency to block PKC. The PKC inhibitors bisindolylmaleimide (BIM) and staurosporin blocked the PMA induced increase in $Ca^{2+}$. The $EC_{50}$ for PMA at either rat or human recombinant VR1 was 90 nM. Cells were challenged with 300 nM PMA (~$EC_{80}$) after 3 min in the indicated antagonist. The, active phorbol ester effect was blocked by RR and CPZ and required extracellular $Ca^{2+}$. CPZ was more potent at the recombinant human compared to the rat receptor.

Anandamide. Anandamide is a brain-derived cannabinoid ligand that acts as a near full agonist at VR1 at low μM concentrations [Smart, 2000 #507]. The $EC_{50}$ of anandamide at recombinant rat and human receptors was 5 μM and 3 μM, respectively. The $IC_{50}$ was determined near the $EC_{80}$ of anandamide (10 μM).

Reactive oxygen species: Disturbances in the regulatory activities of free radicals may play a role in inflammation [Winrow, 1993]. Reactive oxygen species (ROS) such as $H_2O_2$ are formed in inflamed joints. $H_2O_2$ directly activates VR1: the increase in intracellular $Ca^{2+}$ is in part blocked by VR1 antagonists and the response is dependent on extracellular $Ca^{2+}$. The influx of $Ca^{2+}$ through VR1 may contribute to the known effects of ROS on signal transduction (e.g., phosphorylation of proteins) and downstream regulation of gene transcription. The $EC_{80}$ for $H_2O_2$-induced $Ca^{2+}$ flux in VR1/HEK cells was 0.015% $H_2O_2$ and this concentration was used to determine the $IC_{50}$ of VR1 antagonists.

Reducing agents: The reducing agent DTT also directly activates VR1 [Vyklicky, 2002]. Cells were challenged with 5–10 mM DTT to stimulate VR1 after 3 min incubation in compound.

TABLE 3

Antagonism of recombinant human VR1 activated by a panel of stimuli in a $Ca^{2+}$ influx in vitro assay ($IC_{50}$ in nM)

| Compound | Low pH (nM) | Anandamide (nM) | PKC phosphorylation (nM) | PKC phosphorylation at low pH (nM) | $H_2O_2$ reactive oxygen species (nM) |
|---|---|---|---|---|---|
| Capsazepine (CPZ) | 110 | | 160 | 370 | |
| Ruthenium Red (RR) | 500 | | 500 | | |

The reference compounds used in these studies were the previously characterized VR1 antagonists capsazepine (CPZ) and ruthenium red. CPZ, previously the most potent antagonist at human VR1, shows similar potency (100–300 nM) at the human recombinant receptor to inhibit $Ca^{2+}$ activity induced by these stimuli (FIG. 1, left set of panels). For FIG. 1, human (left) and rat (right) vanilloid 1 receptor expressed in HEK 293 cells was stimulated by a number of different stimuli known to activate VR1. FIG. 1 shows the $IC_{50}$ values of the competitive vanilloid antagonist capsazepine for inhibition of the calcium flux induced by each of these activators. Note the similar potency of the compound at the human receptor stimulated by various stimuli, but the lower potency of the compound as an inhibitor of rat VR1.

CPZ has been shown to have significantly lower potency at the rat receptor (recombinant and native receptors; [McIntyre, 2001]). Since many of our animal models were in rat, we cloned the rat VR1 and expressed it stably in HEK293 cells. We performed assays similar to those described for the human recombinant receptor with the exception that a lower pH was required in the $Ca^{2+}$ influx assay at the rat recombinant receptor.

As expected based on data from the literature, the CPZ profile revealed low potency against heat-induced responses at the recombinant rat receptor [Nagy, 1999].

TABLE 4

Antagonism of recombinant rat VR1 activated by a panel of stimuli in the $Ca^{2+}$ influx in vitro assay ($IC_{50}$ in nM)

| Compound | Low pH (nM) | Anandamide (nM) | PKC phosphorylation (nM) | PKC phosphorylation at low pH (nM) | $H_2O_2$(NM) |
|---|---|---|---|---|---|
| Capazepine (CPZ) | 5000 | 1300 | 10000 | 10000 | |
| Ruthenium Red (RR) | | 1860 | | 300 | |

HEK293 Cells expressing human VR1 were grown on poly-D-lysine coated 96 well black-walled plates (BD 354640) and 2 days later loaded with Fluo-3/AM for 1 hour and subsequently tested for agonist-induced increases in intracellular $Ca^{2+}$ levels using FLIPR™ technology. Cells were challenged with test compounds (at varying concentrations) and intracellular $Ca^{++}$ was measured for 3 min prior to the addition of capsaicin to all wells to achieve a final concentration of 0.015 µM eliciting ~80% maximal response. $EC_{50}$ or $IC_{50}$ values were determined from dose-response studies.

TABLE 2

Vanilloid In vitro assay data

| | Receptor binding | | In vitro functional assays | |
|---|---|---|---|---|
| Cmpd No. | % Inhibition @ 1 µM | Ki (nM) | $hIC_{50}$ or $EC_{50}$ (nM) | Estimated $pA_2$ (rat, nM) |
| 1 | | 12.6 | 8 | |
| 2 | | 41.2 | 19 | |
| 3 | | 88.7 | 36 | |
| 4 | | 6.87 | 3.1 | |
| 5 | | 8.87 | 4 | |
| 6 | | 31 | 5.6 | |
| 7 | | 22.7 | 11 | |
| 8 | | 12.9 | 18 | |
| 9 | | 39 | 9.4 | |
| 10 | | 578 | 750 | |
| 11 | | 5.89 | | |
| 12 | | 5.62 | | |
| 13 | | 0.12 | 20 | |
| 14 | | 3.27 | 4.9 | |
| 15 | 11 | | 3700 | |
| 16 | | 0.11 | 27 | |
| 17 | | 0.10 | 4 | |
| 18 | | 93.5 | 45 | |
| 19 | | 0.38 | 26 | |
| 20 | | 0.82 | 6.2 | |
| 21 | | 1290 | 680 | |
| 22 | | 1.28 | 3.3 | |
| 23 | | 53.5 | | |
| 24 | | 1110 | 10000 | |
| 25 | | 3280 | 30000 | |
| 26 | | 18600 | 10000 | |
| 27 | | 1.22 | 97 | |
| 28 | | 100000 | 30000 | |
| 29 | | 36.1 | 44 | |
| 30 | | 581 | | |
| 31 | | 2.03 | 15 | |
| 32 | | 2540 | 30000 | |
| 33 | | 0.26 | 2.7 | |
| 34 | | 1440 | 1000 | |
| 35 | | 1.3 | 5.8 | |
| 36 | | 22.4 | 19 | |
| 37 | | 193 | 45 | |
| 38 | | 6.03 | 11 | |
| 39 | | (rat)382 | | |
| 40 | | (rat)349 | | |
| 41 | | (rat)100000 | | |
| 42 | | 7.22 | | |
| 43 | | (rat)100000 | | |
| 44 | | (rat)100000 | | |
| 45 | | (rat)100000 | | |
| 46 | | (rat)100000 | | |
| 47 | | 2.79 | | |
| 48 | (rat)18 | | | |
| 49 | (rat)1 | | | |
| 50 | 70 | | | |
| 51 | (rat)1 | | | |
| 52 | (rat)1 | | | |
| 53 | (rat)1 | | | |
| 54 | (rat)17 | | | |
| 55 | | 7.35 | | <30 |
| 56 | 93 | | | |
| 57 | | 1.14 | | ~10 |
| 58 | | 5.16 | | |
| 59 | | 7340 | | |
| 60 | 1 | | 30000 | |
| 61 | | 786 | 580 | |
| 62 | 23 | | 30000 | |
| 63 | 37 | | 5800 | |

TABLE 2-continued

Vanilloid In vitro assay data

| Cmpd No. | Receptor binding | | In vitro functional assays | |
|---|---|---|---|---|
| | % Inhibition @ 1 μM | Ki (nM) | hIC$_{50}$ or EC$_{50}$ (nM) | Estimated pA$_2$ (rat, nM) |
| 64 | | 211 | 10000 | |
| 65 | | 129 | 10000 | |
| 66 | | 4.22 | | <100 |
| 67 | 67 | | | |

Example 4

Electrophysiologic Functional Assay Using Dissociated Rat DRG Cells

Compounds are tested for their activity on VR1 expressed endogenously on small rat dorsal root ganglion (DRG) neurons. DRG neurons from normal rats were dissociated (see methods in Chaplan et al., 2003) and whole cell currents mediated by VR1 were recorded using the whole cell patch clamp technique. The estimated potency of the compounds is determined either 1) by measuring the shift in the capsaicin-induced dose response in the presence of compound or 2) by calculating the percent of capsaicin-induced current responses in the presence of compound under conditions of limited capsaicin-induced desensitization (i.e., using 0 $Ca^{2+}$-containing saline solutions).

Under these conditions, repeated application of capsaicin produced similar current responses when 3 min recovery/washout periods were allowed. Briefly in the first method, if a cell was responsive to 300 nM capsaicin (~$EC_{20}$), compound was applied to the cell at 100 or 300 or 1000 nM to determine if the compound had intrinsic agonist activity and allow a 4–5 min incubation period prior to testing with capsaicin in the presence of compound. After 4–5 min exposure to compound, 1 μM capsaicin was applied in the presence of the same concentration of compound and incubated another 2–3 min. This was followed by application of 10 μM CAP in the presence of compound. Control cumulative capsaicin dose response curves (filled squares) were obtained from a cell (the approximate $EC_{50}$ in this cumulative dose response assay was ~1 μM CAP; 10 μM causes a maximal response). Vehicle caused no shift in the capsaicin concentration dependence (not shown). The ability of 1 and 10 μM CAP to cause an increased current after exposure to a compound of the invention was compared to controls.

In the second method, a nociceptor was challenged with 0.3 μM capsaicin while taking measurements of whole cell current using voltage ramp protocols. After washout of the capsaicin, cells were exposed to the compound for 4–5 min and subsequently challenged with 1 μM capsaicin (approximately the ED80 at the native receptor in this experiments) in the continued presence of compound. The current elicited near −100 mV was measured during the first and second capsaicin exposure. The percent of the response elicited by 0.3 μM capsaicin obtained during the exposure to 1 μM capsaicin/compound was calculated. After washout, the cell was challenged with 10 μM capsaicin in the presence of compound and subsequently washed again and challenged with capsaicin without compound.

Example 5

Carrageenan Paw-induced Thermal Hyperalgesia

Each rat is placed on a heated surface (51° C.) in order to measure the time necessary to elicit a response, and an initial (baseline) response time to a thermal stimuli was recorded for each animal. A response is defined as any shaking, licking, or tucking of the treated paw or jumping. Animals not treated with a test compound respond in approximately 20 seconds. The maximal exposure time permitted is 60 seconds to prevent tissue damage. Rats were injected with an irritant (e.g., 1% carrageenan solution in 0.9% saline) subcutaneously into the sub-plantar tissue of the left hind paw to stimulate an acute inflammatory reaction.

Two hours later, the response time of the animal to the thermal stimulus was evaluated and compared to the animal's baseline response time. This shorter response time was recorded as percent hyperalgesia (% H). A cut-off value for % H (usually 75%) was used during analysis to ensure that the animals were hyperalgesic. Animals were then dosed with test drug or vehicle.

At some time(s) later (typically 45 and 90 minutes), the response time of the animal to the thermal stimulus was again evaluated. For each time point, a percent reversal of hyperalgesia (% R) was calculated using the following formula: % R=(Drug Latency−Carrageenan latency)/(Baseline latency−Carrageenan latency). $ED_{50}$ values were calculated from % R obtained at several drug doses.

| Cmpd No | CgHP $ED_{50}$ (mg/kg, po) |
|---|---|
| 33 | 0.276 |
| 57 | 0.354 |
| 4 | 0.804 |
| 17 | 19.958 |

Example 6

Evaluation of Action on Isolated Guinea Pig Bronchial Rings

Aminotetralin VR1 antagonists were tested for their potency to block capsaicin-induced guinea pig bronchial ring contraction in a standard in vitro organ bath assay [Tucker, 2001]. Two mm rings of bronchial tissue obtained from male guinea pigs (325 g) were suspended in normal Krebs solution between two wire hooks under an initial loading tension of 1 gram. The saline was maintained in a 5% $CO_2$ and 95% $O_2$ atmosphere at 37° C. in the presence of indomethacin (5 μM). A sub-maximal dose of 5-Methylfurmethide (5Mef, 1 μM) was added to each tissue to determine responsiveness using an isometric force transducer. After washout, tissues were exposed to compounds or vehicle for 30 min, treated with thiorphan (10 μM, 5% $Na_2CO_3$), and primed using KCl in increasing linear concentrations from 1 mM at 1 mM intervals until a slight increase in muscle tone was induced (~1% of 5Mef response). A concentration-response curve was then constructed using capsaicin (10 nM-10 μM) increasing in 0.5 log unit increments. The dose response curve was calculated as % max of the 5-Mef response and estimated $pA_2$ were determined [Tucker, 2001]).

Compound 33 had a $pA_2$ value of 13 nM against capsaicin-induced contraction in this test.

Example 7

Antitussive Efficacy of VR1 Antagonists

The antitussive activity of intraperitoneally (IP) administered compound is assessed at a single dose level against casaicin-induced cough responses as compared to positive and vehicle controls. Thirty-six male Dunkin-Hartley guinea pigs (295–590 g, mean 425 g) are randomly allocated to one of three groups (n=12 guinea pigs per group). The blinding code is not revealed to the experimenter until coughs from all animals are tallied. Guinea pigs are dosed IP at −60 min with vehicle (15% Solutol in 5% dextrose solution); the positive control codeine (25 mg/kg), or test compound (20 mg/kg in 15% Solutol in 5% dextrose solution). Individual guinea pigs are placed in an exposure chamber with an airflow of 3 L/min at −10 min to acclimatize. At ±0 min, cough responses are induced by exposure to capsaicin aerosol (15 μM) generated by an ultrasonic nebulizer at a nebulization rate of 0.6 ml/min for 4 min. Coughs are counted throughout the 4 min capsaicin exposure and for a further 11 min. The mean±SEM number of capsaicin-induced cough responses recorded in vehicle pre-treated guinea pigs was 3.0±0.5. This level of response was reduced significantly to 0.58±0.15 coughs in codeine pre-treated guinea pigs (P<0.001) and is reduced in compound pre-treated guinea pigs. ANOVA statistical analysis was used to determine the level of significance.

The antitussive properties of test compounds are assessed in a citric acid-induced cough model as compared to positive and vehicle controls. Evaluation of a given compound in this paradigm is as follows: Six male Dunkin-Hartley guinea pigs (approximately 300–600 g) are randomly assigned to each treatment group. Guinea pigs are intra-peritoneally (IP) injected with vehicle, test compound, or positive control (codeine 25 mg/kg) 60 minutes prior to citric acid exposure. Individual guinea pigs are placed in an exposure chamber with an airflow of 3 L/min at −10 min to acclimatize. At ±0 min, cough responses are induced by exposure to nebulized citric acid. Coughs elicited during the 10-minute aerosol of citric acid and additional 5-minute observation period are recorded and analysed for onset of cough, and cough number and frequency. To eliminate bias, pre-treatments are randomised and the experiments are done blinded. The blinding code is not revealed to the experimenter until coughs from all animals are tallied.

Example 8

Rodent Colitis Model

5% Dextran Sulfate Sodium administered in the drinking water of mice or rats for 7 days results in an acute colitis with some morphological changes that are similar to human ulcerative colitis. Among those changes are colon shortening, accumulation of neutrophils and other inflammatory cells, decreases in colon weight, decreases in body weight, tissue damage in the colon, and loss of stool consistency.

Each animal is dosed daily in the morning and late afternoon for BID dosing. Treatment with vehicle or test compound begins on day 0, immediately after initial body weights are taken, and ends on day 6. Water bottles are removed and replaced by graduated water bottles containing 5% DSS in indicated groups. Tap water remains on control groups only. Sufficient DSS drinking water is placed in graduated water bottles and refilled each day to monitor daily output. Animals are weighed daily from day 0 to 7, and animal condition and the consistency of stools recorded. Following sacrifice of the animal on day 7, the colon is surgically removed from the distal rectum (anus) to the cecal-colonic juncture and the colon length and weight measured. Colon slices may be obtained for histological evaluation. An active drug should decrease or eliminate disruption of the epithelium and colonic folds, dense inflammatory cell infiltrates, mucosal sloughing, etc. In life observations include monitoring for signs of gross toxicity and/or behavioral changes, gross evaluation of the skin and fur, motor activity and any behavioral patterns with special attention to tremors, convulsions and diarrhea. Water consumption and body weights are measured daily. Scores include ratings for colon weight loss, stool consistency, colon damage, and colon shortening, and are used to assemble a Disease Activity Score. An increase in myeloperoxidase activity occurs in this model and is evaluated separately.

In a preliminary study, Example 33 did not protect against colon weight loss or colon shortening induced by this model.

Example 9

Uterine Pain Assessment

Female adult virgin Sprague Dawley rats (190–290 g) are used. Rats are anesthetized with pentobarbital (50 mg/kg IP). One uterine horn is approached via a small ventral midline laparotomy and tightly ligated at its caudal end near the cervix with 3.0 silk suture to prevent leakage of mustard oil through the cervix and vagina. Using a 22 G needle 0.1–0.2 ml of 10% mustard oil (Aldrich Chemical Co., Milwaukee Wis. USA; dissolved in mineral oil) or an equivalent volume of saline in sham control rats, are injected into the uterine lumen. The abdominal incision is then closed and the rats allowed to recover from anesthesia. Rats are then transferred to individual Plexiglas cages in a quiet environment (12/12 h light-dark cycle) with food and water ad libitum for nonstop videotape recording for the duration of the experiment. Compounds or vehicle is administered by the intended route before (therapeutic) or after (prophylactic) acquisition of hyperalgesia. The recording system consists of a camera connected to a videotape recorder with a wide range of recording and reading speeds to allow for detailed analysis of the movements of the rats. During the dark phase an infrared light is used to permit continuous filming. Animal behavior is analyzed post-hoc using a scoring system to count abnormal behaviors. Six characteristic abnormal behaviors are expected in uterine inflammation rats: (1) hunching (2) hump-backed position (3) repeated licking of the lower abdomen/ipsilateral flank (4) repeated waves of contraction of the ipsilateral oblique musculature with inward turning of the ipsilateral hind limb (5) stretching of the body (6) squashing of the lower abdomen against the cage floor. The effect of administered compounds on the intensity and frequency of pain related behaviors is quantitatively assessed.

Example 10

Models of Itch, Contact Dermatitis, Eczema and Other Manifestations of Dermal Allergy, Hypersensitivity and/or Inflammation Vanilloid receptor modulators are tested in an animal model of contact dermatitis or itch, according to previously documented and validated methods, including but not limited to those described by Saint-Mezard et al. (2003), Gonzalez et al. (2001), Wille et al. (1998), Weisshaar et al. (1999) and Thomsen et al. (2002). In models of contact dermatitis, testing is conducted in mouse, guinea pig or human in response to a single (primary allergic dermatitis) or repeated (sensitized allergic dermatitis) topical or photomechanical exposure of the skin to one or more haptensselected from 12-myristate-13 acetate, picryl chloride, oxazolone, capsaicin, arachidonic acid, lactic acid, transretinoic acid or sodium lauryl sulfate. For increased sensitivity, animals are sensitized by pre-exposure to certain agents selected from dinitrochlorobenzene, para-phenylenediamine or oxazolone. For prophylactic or therapeutic testing, a vanilloid receptor modulator or vehicle control is administered to the test subjects by the enteral or parenteral route prior to or following hapten challenge. Significant differences in skin inflammation (erythema, edema, hyperthermia, etc.) for the test compound-treated subjects compared with vehicle-treated subjects demonstrate anti-allergy activity. The following additional dependent measures are also collected and compared: skin and/or lymph node levels of CF8+ T cells, interleukin-1 alpha and beta, tumor necrosis factor alpha, interferon gamma, nitric oxide, inducible nitric oxide synthase and keratinocyte apoptosis, Fas expression and/or inflammatory mediator secretion.

In models of itch, testing is conducted in mouse, rat, guinea pig or human in response to the sub- or intra-dermal injection or iontophoresis of pruritogens select4ed from serotonin, compound 48/80, leukotriene B4, arachidonic acid, prostaglandin E2, histamine, substance P, neurokinin A, neurokinin B, trypsin, hydroxyethylstarch or platelet-activating factor singly or in combination with mosquito bite or injection of salivary gland extract therefrom. In some cases, animals are inflamed by pre-exposure to certain agents, including but not limited to sodium lauryl sulfate. For prophylactic or therapeutic testing, a vanilloid receptor modulator or vehicle control is administered to the test subjects by the enteral or parenteral route prior to or following pruritogen challenge. Cumulative scratching behavior and/or number of scratches per unit time are measured. Significant differences in scratching behavior for the test compound-treated subjects compared with vehicle-treated subjects demonstrate anti-pruritic activity. The following additional dependent measures are collected and compared: skin inflammation (erythema, edema, hyperthermia, etc.), surface area of the wheal and flare, hyperalgesia, allodynia, plasma protein extravasation, inflammatory mediator release and serum immunoglobulin levels.

Example 11

Models of Rhinitis, and Other Manifestations of Nasal Hypersensitivity and/or Inflammation Vanilloid receptor modulators are tested in an animal model of rhinitis, according to previously documented and validated methods, including but not limited to those described by Hirayama et al. (2003), Tiniakov et al. (2003) and Magyar et al. (2002). Testing is conducted in mouse, guinea pig, dog or human in response to intranasal challenge with one or more irritants selected from bradykinin, histamine, pollens, dextran sulfate, 2,4-tolylene diisocyanate, *Bordetella bronchiseptica*, *Pasteurella multodica* or acetic acid. For increased sensitivity, animals may be sensitized by pre-exposure to ragweed or ovalbumin. For prophylactic or therapeutic testing, a vanilloid receptor modulator or vehicle control is administered to the test subjects by the enteral or parenteral route prior to or following irritant challenge. The relevant dependent measures collected are plasma extravasation of the nasal mucosa, nasal eosinophilia or neutrophilia, nasal mucosal or nasal cavity lavage fluid levels of IL-5, interferon gamma, histamine or IgE, serum immunoglobulin levels, rhinorrhea, cumulative time spent sneezing or number of sneezes per unit time, nasal airway volume, peak inspiratory flow and resistance, intranasal pressure and nasal lesions. Significant differences in one or more of these measures for the test compound-treated subjects compared with vehicle-treated subjects demonstrate anti-rhinitis activity.

Example 12

Models of Anxiety, Panic Disorder and Other Non-Adaptive Stressful or Phobic Responses Vanilloid receptor modulators are tested in an animal model of anxiety, according to previously documented and validated methods, including but not limited to those reviewed by Imaizumi and Onodera (2000). Testing is conducted in mouse or rat and consists of methods to measure avoidance of aversive environmental stimuli selected from the Geller-type or Vogel-type anticonflict tests, the light/dark test, the hole-board test, the elevated plus-maze and the elevated T-maze. Prior to environmental exposure the test subject receives the prophylactic administration one or more times of a vanilloid receptor modulator, or vehicle control, by the enteral or parenteral route. The cumulative time or number of times spent engaged in the aversive behavior is measured. Significant differences in one or more of these measures for the test compound-treated subjects compared with vehicle-treated subjects are taken as evidence of anxiolytic activity.

Example 13

VR1 Modulator Activity in a Rat Hot Flash Model

Vanilloid receptor modulators are tested in a rat model for hot flush/hot flash. Triggers that cause a rise in skin temperature include vagal afferent input and temperature control centers in the hypothalamus (e.g., preoptic area). An animal model of hot flush has been developed using morphine-dependent, ovariectomized rats in which precipitated withdrawl by the morphine antagonist naloxone produces effects similar to those experienced by menopausal women (Simpkins, J W et al., 1983 Life Science 32: 1957; Katovich, M J et al., 1986 8:67; Merchenthaler, I et al., 1998 Maturitas 30:307). Measured effects are a decrease in core body temperature and an increase in tail skin temperature, effects that show some similarities to systemic administration of capsaicin, an exogenous agonist at the vanilloid VR1 receptor. The physiological events observes in the rat model for hot flush is similar in magnitude and duration to human hot flush episodes. Hot flushes have been linked to a transient disruption of the thermoregulatory mechanism that activates a heat-loss responses consisting of sweating and increased peripheral blood flow (Kronenberg, et al., 1984 Maturitas 6: 31; Berendsen, 2000 Maturitas 36: 155).

60 day old female Sprague-Dawley rats are ovariectomized and treatments begin at least 7 days later. The assay described here is a modification of that described (Merchenthaler, I et al., 1998 Maturitas 30:307). Animals are housed under 12 hour light/dark cycle and provided food and water ad libitum. A morphine pellet (75 mg) is implanted subcutaneously on day 1 and and 2 pellets are implanted at day 5. Ten animals are in each treatment group. On the 8th day, each group is injected with ketamine (80 m/kg, im) to lightly anesthetize the animals in an effort to avoid animal restraint and stress induced responses, and an external thermocouple is taped to the tail 1 inch from the root of the tail and connected to an ADC and computer. Data are collected continuously. After 15 min of baseline recordings, VR1 modulators or vehicle are administered po and 30 min later, naloxone-precipitated withdrawl is evoked by naloxone (1 mg/kg sc (0.2 ml). The tail temperature is recorded for a further 60 min. The peak of the temperature rise is compared in vehicle and VR1-modulator treated groups. The results are evaluated according to Merchenthaler, I et al., 1998 (Maturitas 30:307).

As an alternative, tail temperatures can be measured telemetrically according to Berendsen et al., 2001 (Eur J Pharmacology 419: 47). Ovariectomized or sham operated animals are implanted with a temperature and physical activity transmitter (TA10TA-F40; Data Sciences International) under isoflurane anaesthesia. The body of the transmitter is placed in the peritoneal cavity through a ventral laparotomy and stitched to the abdominal muscles. The temperature probe is adapted for placement on the rat's tail as described (Berendsen et al., 2001).

REFERENCES

Simpkins, J W et al., 1983 Life Science 32: 1957;
Katovich, M J et al., 1986 8:67;
Merchenthaler, I et al., 1998 Maturitas 30:307
Kronenberg, et al., 1984 Maturitas 6: 31.
Berendsen, H. H. G. 2000 Maturitas 36: 155
Berendsen H. H. G. et al., 2001 Eur J Pharmacology 419: 47

What is claimed is:
1. A compound comprising a compound of Formula (Ia):

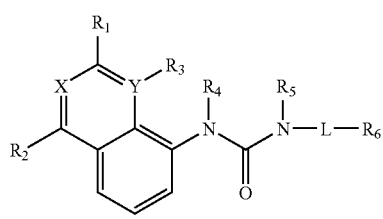

Formula (Ia)

wherein the compound is selected from the group consisting of:
a compound of formula (Ia) wherein $R_1$ is H, $R_2$ is H, $R_3$ is H, $R_4$ is H, $R_5$ is H, L is —$CH_2CH_2$—, $R_6$ is (4-Cl)Ph, X is N, and Y is C;
a compound of formula (Ia) wherein $R_1$ is H, $R_2$ is H, $R_3$ is H, $R_4$ is H, $R_5$ is H, L is —$CH_2$—, $R_6$ is (3-$CF_3$)Ph, X is N, and Y is C;
a compound of formula (Ia) wherein $R_1$ is Me, $R_2$ is H, $R_3$ is H, $R_4$ is H, $R_5$ is H, L is —$CH_2$—, $R_6$ is (3-$CF_3$)Ph, X is N, and Y is C;
a compound of formula (Ia) wherein $R_1$ is H, $R_2$ is H, $R_3$ is H, $R_4$ is H, $R_5$ is H, L is —$CH_2CH((4\text{-}OMe)Ph)$, $R_6$ is Pyridin-3-yl, X is N, and Y is C;
a compound of formula (Ia) wherein $R_1$ is H, $R_2$ is H, $R_3$ is H, $R_4$ is H, $R_5$ is H, L is —$CH_2CH(\text{-}CH_2Ph)\text{-}$, $R_6$ is (4-OMe)Ph, X is N, and Y is C;
a compound of formula (Ia) wherein $R_1$ is H, $R_2$ is H, $R_3$ is H, $R_4$ is H, $R_5$ is H, L is —$CH_2CH(—CH_2\text{cyclohexyl})$—, $R_6$ is (4-OMe)Ph, X is N, and Y is C;
a compound of formula (Ia) wherein $R_1$ is H, $R_2$ is H, $R_3$ is H, $R_4$ is H, $R_5$ is H, L is —$CH_2CH_2$—, $R_6$ is (4-OMe)Ph, X is N, and Y is C;
a compound of formula (Ia) wherein $R_1$ is H, $R_2$ is H, $R_3$ is H, $R_4$ is H, $R_5$ is H, L is —$CH_2CH_2$—, $R_6$ is Ph, X is N, and Y is C;
a compound of formula (Ia) wherein $R_1$ is H, $R_2$ is H, $R_3$ is H, $R_4$ is H, $R_5$ is H, L is —$CH_2CH_2$—, $R_6$ is (4-t-Bu)Ph, X is N, and Y is C;
a compound of formula (Ia) wherein $R_1$ is H, $R_2$ is H, $R_3$ is H, $R_4$ is H, $R_5$ is H, L is —$CH_2CH_2$—, $R_6$ is (4-$CF_3$)Ph, X is N, and Y is C;
a compound of formula (Ia) wherein $R_1$ is H, $R_2$ is H, $R_3$ is H, $R_4$ is H, $R_5$ is H, L is —$CH_2$—, $R_6$ is (4-OMe)Ph, X is N, and Y is C;
a compound of formula (Ia) wherein $R_1$ is H, $R_2$ is H, $R_3$ is H, $R_4$ is H, $R_5$ is H, L is —$CH_2CH_2$—, $R_6$ is (4-$OCF_3$)Ph, X is N, and Y is C.
2. A composition comprising a compound of Formula (II):

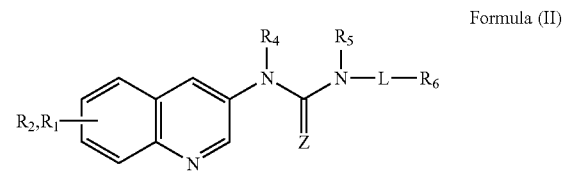

Formula (II)

wherein the compound is selected from the group consisting of:
a compound of formula (II) wherein $R_1$ is H, $R_2$ is H, $R_4$ is H, $R_5$ is H, L is $R_6$ is (3-$CF_3$)Ph, and Z is O;
a compound of formula (II) wherein $R_1$ is H, $R_2$ is H, $R_4$ is H, $R_5$ is H, L is —$CH_2$—, $R_6$ is (4-$CF_3$)Ph, and Z is O;
a compound of formula (II) wherein $R_1$ is H, $R_2$ is H, $R_4$ is H, $R_5$ is H, L is —$CH_2$—, $R_6$ is (3,4-diCl)Ph, and Z is O;
a compound of formula (II) wherein $R_1$ is H, $R_2$ is H, $R_4$ is H, $R_5$ is H, L is —$CH_2CH_2$—, $R_6$ is (3,4-diCl)Ph, and Z is O;
a compound of formula (II) wherein $R_1$ is H, $R_2$ is H, $R_4$ is H, $R_5$ is H, L is —$CH_2$—, $R_6$ is (4-N(Me)n-pentyl)Ph, and Z is O; and
a compound of formula (II) wherein $R_1$ is H, $R_2$ is H, $R_4$ is H, $R_5$ is H, L is —$CH_2$—, $R_6$ is (4-N(Me)$CH_2$cyclohexyl)Ph, and Z is O.
3. A pharmaceutical composition comprising a compound, salt or solvate according to claim 1 admixed with a pharmaceutically acceptable carrier, excipient or diluent.
4. A veterinary composition comprising a compound, salt or solvate according to claim 1 admixed with a veterinarily acceptable carrier, excipient or dilluent.
5. A pharmaceutical composition comprising a compound, salt or solvate according to claim 2 admixed with a pharmaceutically acceptable carrier, excipient or diluent.

* * * * *